US010661010B1

(12) United States Patent
Tsinberg

(10) Patent No.: US 10,661,010 B1
(45) Date of Patent: May 26, 2020

(54) WEARABLE DEVICE AND METHOD FOR SENSING AND TREATING OPIOID OVERDOSE

(71) Applicant: Mikhail Tsinberg, New York, NY (US)

(72) Inventor: Mikhail Tsinberg, New York, NY (US)

(*) Notice: Subject to any disclaimer, the term of this patent is extended or adjusted under 35 U.S.C. 154(b) by 0 days.

(21) Appl. No.: 16/445,387

(22) Filed: Jun. 19, 2019

Related U.S. Application Data

(63) Continuation-in-part of application No. 16/014,414, filed on Jun. 21, 2018.

(Continued)

(51) Int. Cl.
*G08B 1/08* (2006.01)
*A61M 5/172* (2006.01)
(Continued)

(52) U.S. Cl.
CPC ......... *A61M 5/1723* (2013.01); *A61B 5/0002* (2013.01); *A61B 5/0295* (2013.01); *A61B 5/4839* (2013.01); *A61B 5/726* (2013.01); *A61B 5/746* (2013.01); *A61B 5/7475* (2013.01); *A61B 8/085* (2013.01); *A61M 37/0015* (2013.01); *A61B 5/0816* (2013.01); *A61M 2037/0023* (2013.01); *A61M 2205/18* (2013.01); *A61M 2205/3313* (2013.01); *A61M 2205/3337* (2013.01); *A61M 2205/3375* (2013.01);
(Continued)

(58) Field of Classification Search
CPC ............ A61M 5/1723; A61M 37/0015; A61M 2205/50; A61M 2230/42; A61M 2230/04; A61M 2205/3553; A61M 2205/18; A61M 2205/3569; A61M 2205/3313; A61M 2205/502; A61M 2205/3375; A61M 2205/70; A61M 2037/0023; A61M 2205/3337; A61B 5/0002; A61B 5/0295; A61B 5/7475; A61B 8/085; A61B 5/726; A61B 5/746; A61B 5/4839; A61B 5/0816
USPC ..................................................... 340/539.12
See application file for complete search history.

(56) References Cited

U.S. PATENT DOCUMENTS

2009/0131765 A1 * 5/2009 Roschak .................. A61B 8/06
600/301
2012/0253140 A1 * 10/2012 Addison .............. A61B 5/4035
600/301

(Continued)

OTHER PUBLICATIONS

Kiran Balaji PS, Anand Jatti. "Respiration and Heart Rate Monitoring from Photoplethysmograph Signal", Advances in Signal Processing 3(1): 8-16, 2015 http://www.hrpub.org, DOI: 10.13189/asp.2015.030102.

(Continued)

*Primary Examiner* — Tanmay K Shah
(74) *Attorney, Agent, or Firm* — Arent Fox LLP

(57) ABSTRACT

Disclosed is an implantable medical device configured to detect opioid overdose symptoms, such as a critically low respiratory rate, and automatically release opioid overdose medication into the body of a user. The embedded device may use a ultrasound- or photoplethysmographic-based technique for monitoring the respiratory rate of the user. Additionally, the embedded medical device can communicate with a paired mobile device and automatically contact medical services and/or emergency contacts when opioid overdose is detected.

15 Claims, 15 Drawing Sheets

Related U.S. Application Data

(60) Provisional application No. 62/522,921, filed on Jun. 21, 2017, provisional application No. 62/671,033, filed on May 14, 2018.

(51) Int. Cl.

| | | |
|---|---|---|
| *A61M 37/00* | (2006.01) | |
| *A61B 5/00* | (2006.01) | |
| *A61B 5/0295* | (2006.01) | |
| *A61B 8/08* | (2006.01) | |
| *A61B 5/08* | (2006.01) | |

(52) U.S. Cl.
CPC ............... *A61M 2205/3553* (2013.01); *A61M 2205/3569* (2013.01); *A61M 2205/50* (2013.01); *A61M 2205/502* (2013.01); *A61M 2205/70* (2013.01); *A61M 2230/04* (2013.01); *A61M 2230/42* (2013.01)

(56) References Cited

U.S. PATENT DOCUMENTS

2015/0196257 A1* 7/2015 Yousefi ................. A61B 5/024
 600/324
2018/0147343 A1* 5/2018 Tyson .................... G16H 20/17

OTHER PUBLICATIONS

A. B. Hertzman, "The blood supply of various skin areas as estimated by photoelectric plethysmograph," Amer. J. Physiol., vol. 124, No. 2, pp. 328-340, Oct. 1938.

J. G. Webster, Design of Pulse Oximeters. New York: Taylor & Francis, 1997.

A. Johansson, L. Nilsson, S. Kalman, and P. Ä. Öberg, "Respiratory monitoring using photoplethysmography," in Proc. 20th Annu. Conf. IEEE EMBS, 1998, vol. 20, No. 6, p. 3226.

J. Li, J. Jin, X. Chen, W. Sun, and P. Guo, "Comparison of respiratoryinduced variations in photoplethysmographic signals," Physiol. Meas., vol. 31, No. 3, pp. 415-425, Mar. 2010.

W. Einthoven, G. Fahr, and A. Waart, "On the direction and manifest size of the variations of potential in the human heart and on the influence of the position of the heart on the form of the electrocardiogram," Amer. Heart J., vol. 40, No. 2, pp. 163-211, Aug. 1950.

R. Bailon, L. Sommo, and P. Laguna, "A robust method for ECG-based estimation of the respiratory frequency during stress testing," IEEE Trans. Biomed. Eng., vol. 53, No. 7, pp. 1273-1285, Jul. 2006.

Mark van Gastel, Sander Stuijk and Gerard de Haan , "Motion robust remote-PPG in infrared", IEEE Transactions on Biomedical Engineering ( vol. 62, Issue: 5, May 2015 ).

* cited by examiner

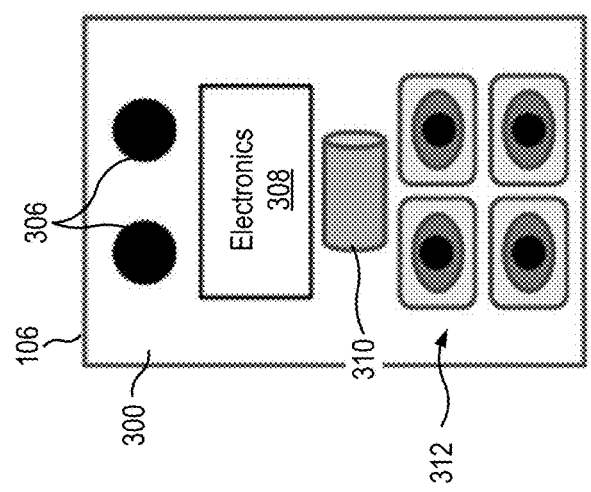
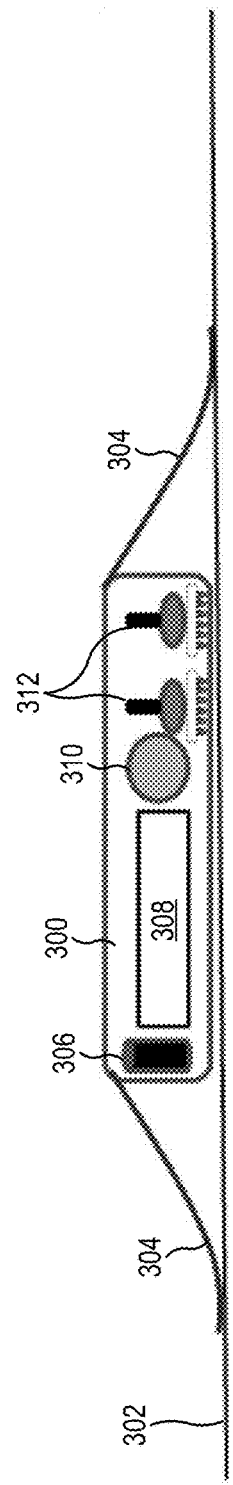
Fig. 3A
Fig. 3B

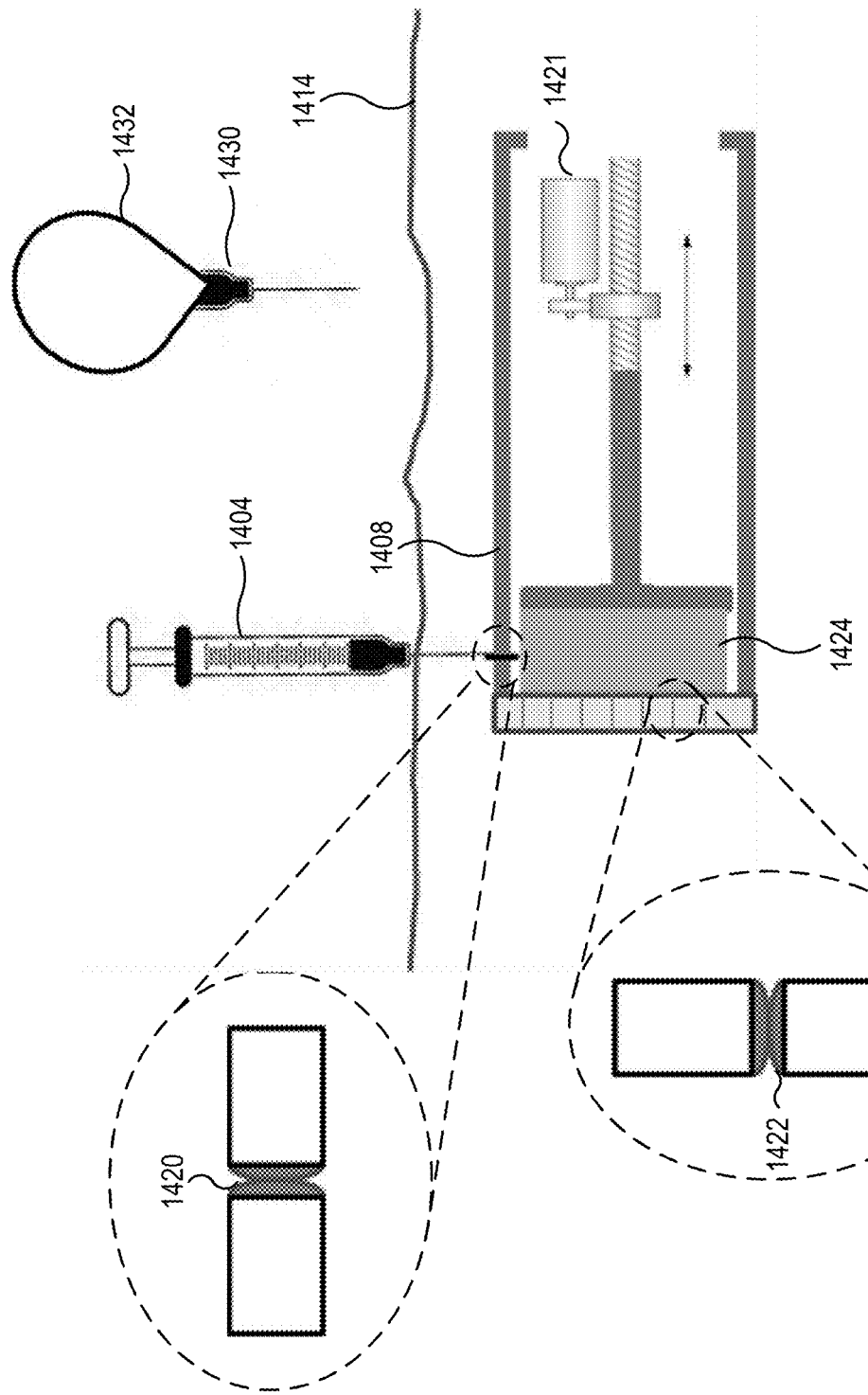

WEARABLE DEVICE AND METHOD FOR SENSING AND TREATING OPIOID OVERDOSE

CROSS-REFERENCE TO OTHER APPLICATIONS

This application is a continuation-in-part application of U.S. application Ser. No. 16/014,414 filed on Jun. 21, 2018, which claims the benefit of U.S. Provisional Application No. 62/522,921 filed on Jun. 21, 2017, and U.S. Provisional Application No. 62/671,033, filed May 14, 2018; all of which are incorporated herein by reference.

BACKGROUND

Opioids, whether used in a clinical or non-clinical environment, are highly addictive and can lead to varying degrees opioid toxicity. Examples of opioids include opium, morphine, codeine, oxycodone, meperidine, fentanyl, hydromorphone, methadone, and propoxyphene. Acute users experience opioid intoxication, wherein the user uses a sufficient amount of an opioid to get a "high". These acute users may experience overdose symptoms (e.g., opioid-induced coma) when too much of an opioid is taken. An overdose of opioids, because of their effect on the central nervous system (which regulates breathing), can lead to respiratory depression (i.e., a person not breathing) and death.

Treatments have been developed that can block the effects of opioids. For example, an opioid antagonist, such as naloxone, can be administered to reverse the effects of opioid intoxication or overdose. The medication and other emergency aid must be administered in time; otherwise, the lack of oxygen will cause irreparable brain damage or death. However, such medications are not widely available, and in many cases are applied too late to be effective. As such, the existing treatments fail to solve the technical problem of administering medication such as opioid overdose antidotes in an effective period of time to address respiratory depression.

SUMMARY

Thus, a system and method is disclosed herein for treating opioid overdose symptoms, and, more particularly, for a wearable medical device that detects instances of opioid overdose or other emergency medical conditions of the wearer and automatically injects the appropriate medication. One technical result of the described system is an improved efficiency and responsiveness in the administration of opioid overdose medication, which increases the likelihood of survival of individuals experiencing opioid overdose. The technical result is achieved using a wearable device that detects opioid overdose using an ultrasound-based sensor and responsively injects the appropriate dosage of opioid overdose medication into the user, absent user intervention.

According to one aspect of the present disclosure, a medical device is provided for treating emergency medical conditions. The medical device includes an ultrasound transducer configured to transmit ultrasound waves through pulmonary issue of a user and generate resulting electrical signals based on received ultrasound waves, and a medicine release unit implanted within the body of the user, wherein the medicine release unit includes a volume of liquid medication. The medical device further includes a processing system configured to determine the respiratory rate of the user based on the resulting signals that indicate a measurement of distances between emitted and reflected ultrasound pulses, and actuate the medicine release unit to release the medication into the body of the user based on a comparison of the respiratory rate of the user with a threshold respiratory rate.

According to another aspect, a medical device for treating emergency medical conditions is provided. The medical device includes a light sensor configured to obtain a photoplethysmographic signal associated with the user and detect a respiratory rate of a user based on the photoplethysmographic signal. The medical device further includes a medicine release unit implanted within the body of the user, wherein the medicine release unit includes a volume of liquid medication. The medical device includes a processing system configured to actuate the medicine release unit to release the medication into the body of the user based on a comparison of the respiratory rate of the user with a threshold respiratory rate.

According to another exemplary aspect, a computer-readable medium is provided comprising instructions that comprises computer executable instructions for performing any of the methods disclosed herein.

The above simplified summary of example aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplarily pointed out in the claims.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

FIG. 3A and FIG. 3B are schematic diagrams illustrating top and side views, respectively, of a wearing device having a respiratory rate sensor and drug injector, according to an aspect of the present disclosure.

FIGS. 14A and 14B are block diagrams of a medical device configured as an embedded module according to one aspect of the present disclosure.

DETAILED DESCRIPTION

Exemplary aspects are described herein in the context of a system, device, and method for treating opioid overdose. Those of ordinary skill in the art will realize that the following description is illustrative only and is not intended to be in any way limiting. Other aspects will readily suggest themselves to those skilled in the art having the benefit of this disclosure. Reference will now be made in detail to implementations of the example aspects as illustrated in the accompanying drawings. The same reference indicators will be used to the extent possible throughout the drawings and the following description to refer to the same or like items.

Figure 1:
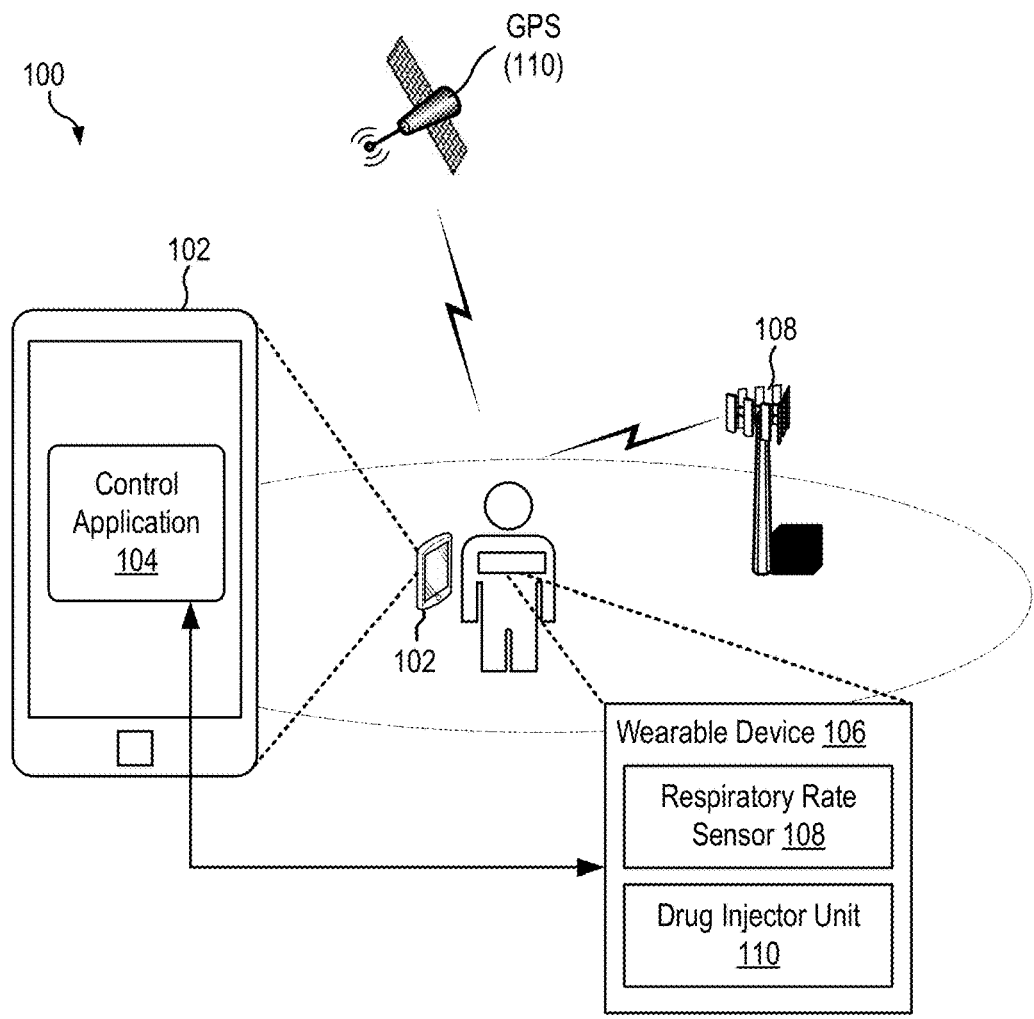
FIG. 1 is a block diagram depicting a system for detecting an opioid overdose based on a user's respiration and administering a medication via an injector unit.

FIG. 1 is a block diagram depicting a system 100 for detecting an emergency medical condition (e.g., opioid overdose) based on a user's respiration and administering a medication via an injector unit. In one embodiment, the system includes a wearable device 106 having a respiratory rate sensor 108 and a drug injector unit 110. The wearable device 106 is configured to monitor the user's respiration using an ultrasound-based system, as described below, or using other suitable systems such as those based on photoplethysmographic sensing techniques (also described below). The wearable device 106 is further configured to inject into the user a dosage of a medication selected to treat the emergency medical condition (for example, in the case of opioid overdose, an opioid antagonist naloxone) based on the monitored respiration of the user. In some embodiments, the injector unit 110 may include one or more microneedle (MN) arrays containing the medication.

The disclosed system and techniques are described herein for use in treating symptoms of overdose on strong pain medicines and other drugs that can hold back breathing (i.e., opioids) for illustrative purposes. It is understood that the aspects of the present disclosure can be used to treat other medical conditions that require instant medication injection based on detected changes in respiratory rate. For example, other medical conditions may include an asthma attack; infant respiratory distress syndrome; lung diseases such as chronic obstructive pulmonary disease (COPD), emphysema, bronchitis, pneumonia, and pulmonary edema (fluid in the lungs); heart problems; anemia (i.e., a low number of red blood cells, which carry oxygen); cyanide poisoning; hypothyroidism; toxins; carbon monoxide poisoning; head injury; use of sedatives or anesthesia; breathing problems during sleep, such as sleep apnea; conditions that affect nerves or muscles involved in breathing, such as Guillain-Barré syndrome or amyotrophic lateral sclerosis (ALS); and respiratory syncytial virus (RSV). Additionally, it is understood that aspects of the present disclosure are not limited to being triggered based on a reduced respiratory rate, and can also be used to detect medical conditions based on increased or irregular respiratory rate. In yet other aspects, the described medical device can be further modified to monitor the heart rate of the user (and instead use the described suppression and extraction techniques to remove the respiratory component from the signals, leaving the heart rate signal components).

Figure 2:
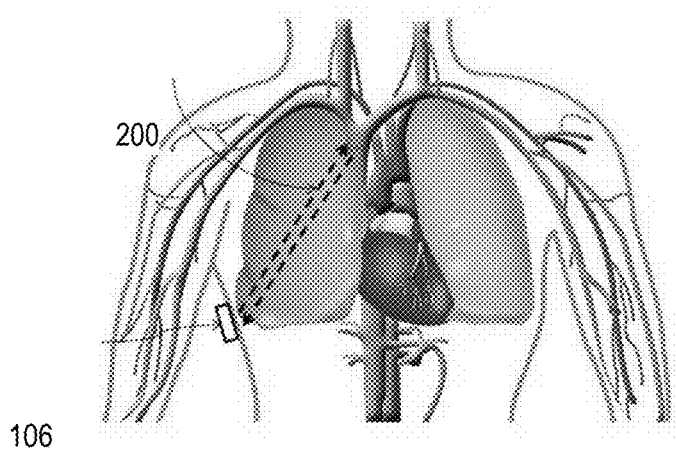
FIG. 2 illustrates an example position for wearing the wearable device shown in FIG. 1.

FIG. 2 illustrates an example position for wearing the wearable device 106 shown in FIG. 1. The wearable device 106 having the respiratory rate sensor 108 and drug injector 110 may be operatively coupled to a portion of the body of the user, depending on the sensing technique employed by the wearable device. For example, for ultrasound-based embodiments, the user may wear the wearable device on a location of their body suitable for transmitting and receiving ultrasonic waves 200 (i.e., ultrasound) to at least one of their lungs, such as the side ribcage of the user's body. The wearable device may be secured to the user's body via adhesive, such as tape, or by other fastening means, such as a belt. In another example, for photoplethysmography-based embodiments, the user may wear the wearable device 106 on a location of their body that has visible access to the user's blood vessels, such as on the user's wrist.

Referring back to FIG. 1, the wearable device 106 may be communicatively coupled to a control device 102 configured to execute a control application 104 (e.g., "Survive OD application") operated by the user. Examples of a control device 102 may be a smartphone, tablet, PDA, smart-watch, and other suitable mobile devices or portable electronics. The wearable device 106 and control device 102 may communicate via a wired connection or via a wireless connection, such as provided by a Bluetooth® connection, radio frequency (RF) connection, or Wi-Fi connection. The control device 102 may be configured to determine the location of the user (e.g., via a GPS component in the control device) and transmit one or more messages based on the status of the respiratory rate sensor and drug injector device to certain parties (e.g., emergency contacts) or entities (e.g., medical services).

The wearable device 106 may be configured to detect when the user's respiration rate has reached a threshold rate (e.g., a low rate) and, in response, use the drug injector to inject the medication into the user (e.g., subcutaneously, or intramuscularly). In some embodiments, the control device 102 may offer the user the ability to intervene, such as through the control application 104, and stop the release of medicine. If the user does not react, the injector releases one of a single-use medicine actuators into the microneedle array and subsequently the medicine into the user's body. In other embodiments, the injector unit may use permanent medicine injectors instead. In cases where the control device is out of reach of the user, turned off, or otherwise unavailable, the wearable device may be self-containing and release actuators for microneedle arrays if the respiratory rate reaches a critical low rate.

Figure 5:
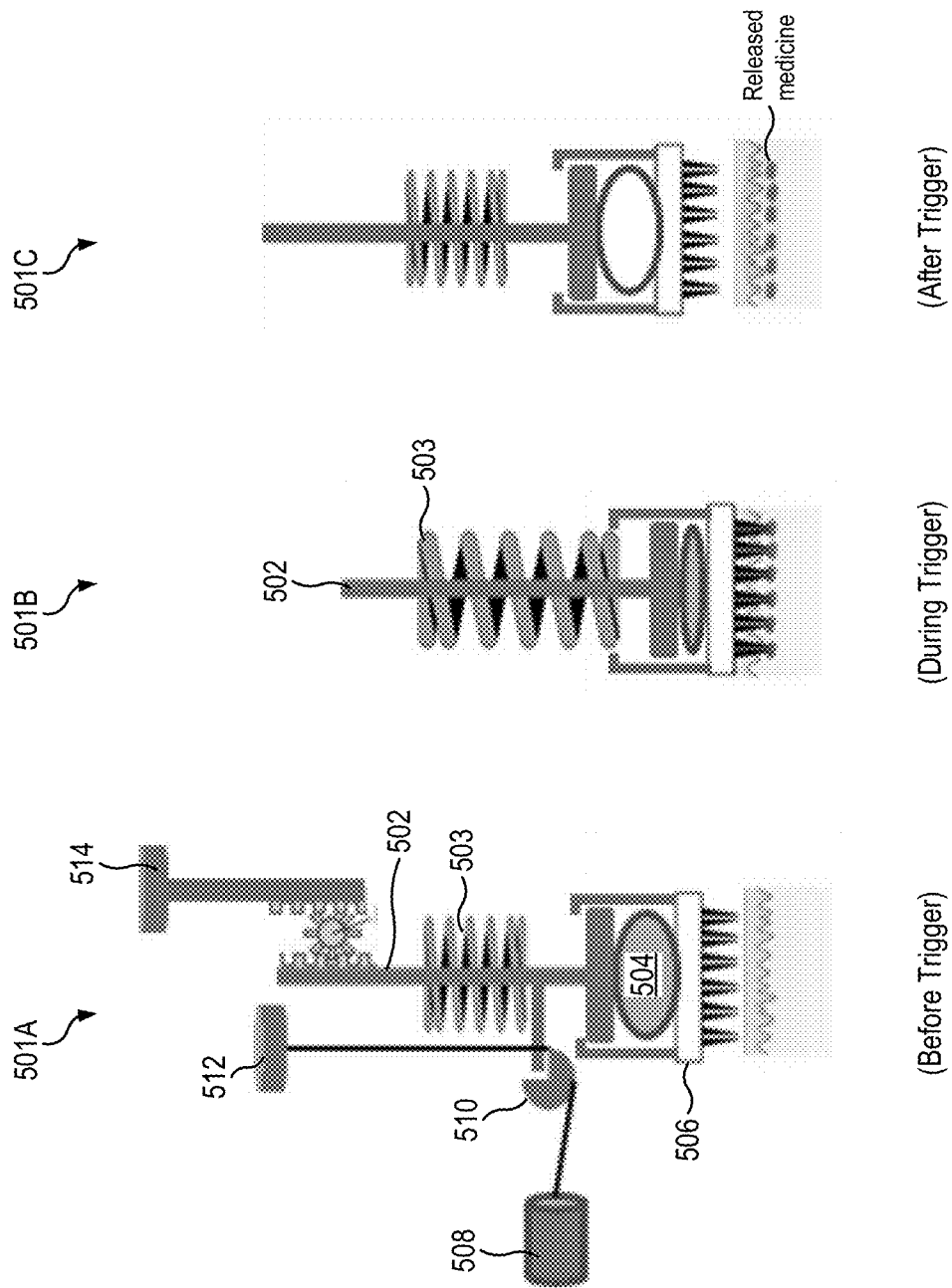
FIG. 5 is a schematic diagram depicting operations of the microneedle injector system according to one embodiment.
Figure 7:
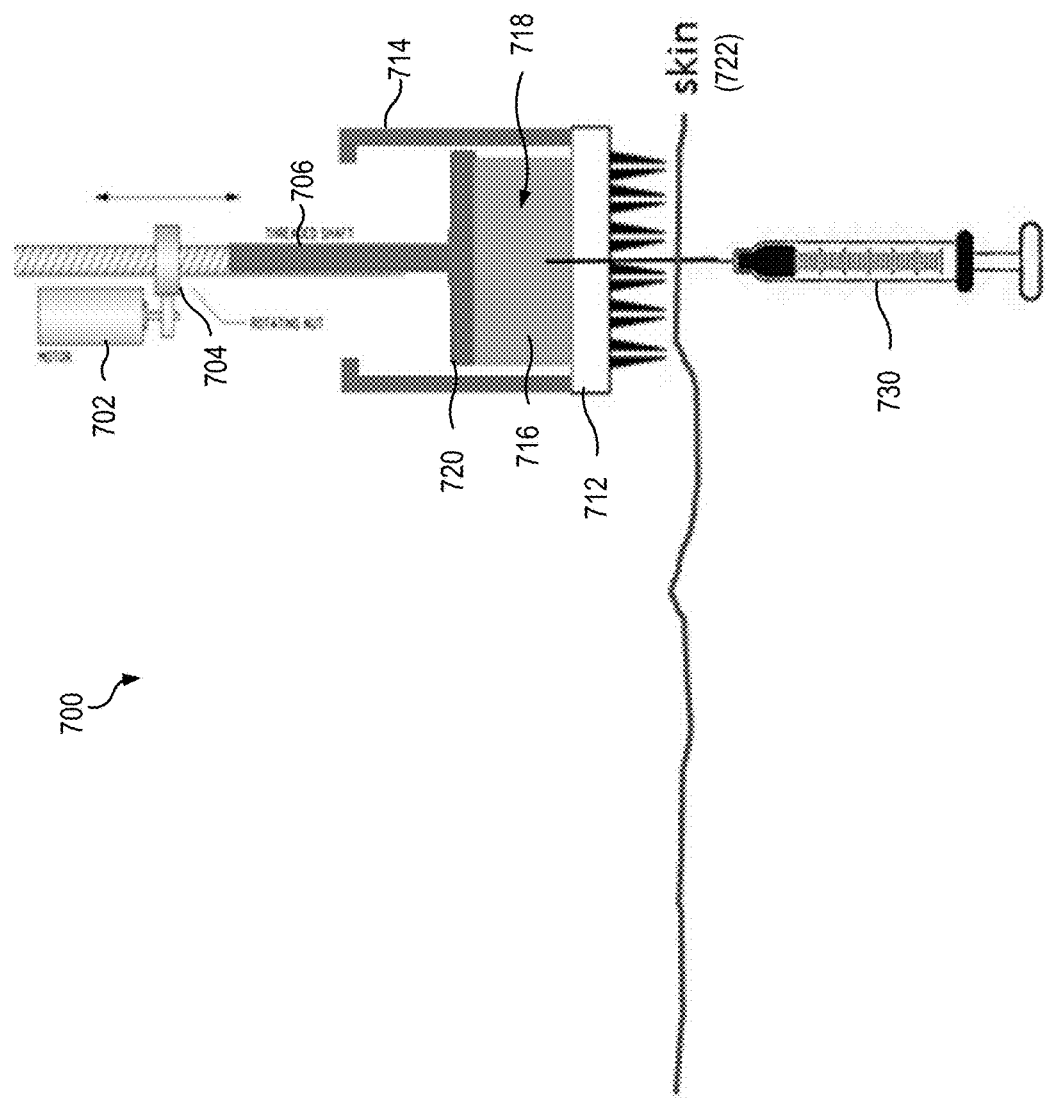
FIG. 7 depicts a medicine release and pullback shaft electric motor based system configured as a permanent injection system according to one embodiment.
Figure 8:
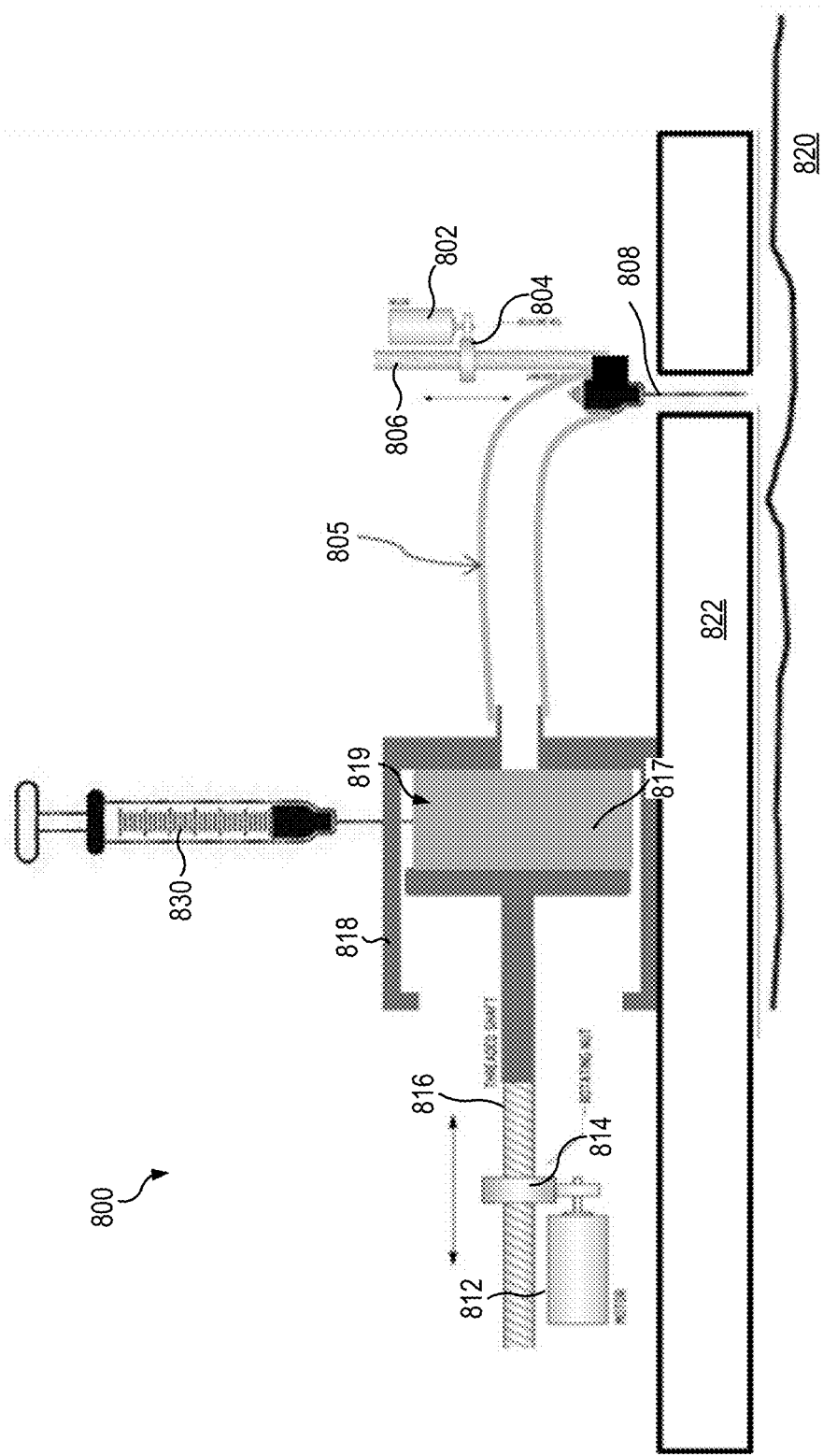
FIG. 8 depicts an alternative embodiment of the permanent injection system configured to perform medicine release and pullback using a dual electric motor based system.

The medicine release mechanism of the drug injector unit can be spring-based mechanical system (as shown in FIG. 5)

or automatic by using small electric motors (as shown in FIGS. 7-8). The medicine release mechanism may further include a manual release mechanism in case the electronics are non-functional (e.g., electronics are not recharged). For example, in the case of a spring-based system, the microneedle array medicine release can also be activated by a manual push button.

In some embodiments, the control application 104 may be configured to register the location of the user (e.g., using a GPS module) and send a warning message to designated relatives, emergency ambulances, monitoring emergency centers, and/or other contacts pre-selected by the user, in response to a triggering condition. In some embodiments, the control application 104 may be configured to monitor the status of the injector unit 110, such as the amount of used and new MN array modules in the unit. If low medication amounts are detected, the control application 104 may alert the user, and optionally a list of users and contacts, about the need to replace or refill the used MN array modules.

FIG. 3A and FIG. 3B are schematic diagrams illustrating top and side views, respectively, of a wearable device 106 having a respiratory rate sensor and drug injector, according to an aspect of the present disclosure. As shown, the wearable device 106 may be secured to a skin surface 302 of the user by a fastener 304. In one aspect, the fastener is configured to operatively couple the wearable device 106 to the body of the user (e.g., connect to bare skin), such that the wearable device is able to perform both sensing techniques and drug-injection actions. In one aspect, the fastener 304 may be a substance (e.g., glue, adhesive, paste) that binds the wearable device to the body of the user, a physical element that mechanically secures the wearable device to the body of the user (e.g., belt, bracelet), some combination thereof (e.g., tape), or other suitable means for fastening.

The wearable device 106 having the respiratory rate sensor and drug injector may include a housing 300 that contains one or more ultrasonic sensors 306, a wireless rechargeable battery 310 that powers the device, various electronics 308 including a wireless modem (e.g., configured to support Bluetooth or Wi-Fi), and one or more microneedle arrays 312 and microneedle capsules with some actuators (e.g., spring or motor) and medicine. In the aspect shown, the respiratory rate sensor and drug injector may be integrated into a single unit, i.e., contained in the same housing 300. It is understood that, in other aspects, a distributed system may be used in which the respiratory rate sensor and drug injector communicatively coupled but are housed in separate elements. For example, the respiratory rate sensor may be housed in a smart-watch device operated by the user, and the drug injector unit is housed in a separate unit.

In one aspect, the ultrasonic sensor(s) 306 (also referred to as ultrasonic transducers) are configured to determine a respiratory rate of a user based on ultrasonic waves reflecting internally within the body of the user. The ultrasonic sensor 306 may include any combination of ultrasonic transmitters (e.g., emitters) which are configured to transmit ultrasound waves through the body of the user (e.g., through the pulmonary tissue), ultrasonic receivers configured to receive reflected ultrasounds and generate resulting electrical signals based on the received ultrasound, or ultrasonic transceivers which can both transmit and receive ultrasound. As described in greater detail below, the ultrasonic sensor 306 may include a processing system that is configured to determine the respiratory rate of the user based on the resulting signals that indicate a measurement of distances between emitted and reflected ultrasound pulses, which is correlated with lung size measurements of the user at a given moment.

In one aspect, the injector unit 110 may include an injector needle configured to administer a liquid medication, such as an opioid antagonist for treating an opioid overdose, into the body of the user, based on signals provided by the electronics 308. In the aspect shown in FIGS. 3A and 3B, the injector unit 110 may include one or more microneedle arrays 312 and microneedle capsules with actuators configured to administer the liquid medication. In some aspects, the microneedle array and the pouch of the injector unit are formed as an integrated unit which can be refilled with medication. In other aspects, the pouch of the injector unit comprises a replaceable single-use unit.

In some embodiments, in the beginning of the wearable device's operations, the device can self-calibrate the ultrasound and size of lung cavity by asking the user (e.g., through the control application) to deeply inhale and exhale. During this calibration process, the wearable device will measure the size of the lung cavity to mask out all the noise signal reflections reaching the ultrasound waves.

In some embodiments, RF systems radar at the frequency of greater than 5 GHz can also be used instead of ultrasound waves in a similar EM radar operation. However, RF travels much faster, and it is more expensive to measure shorter time distances between reflected RF pulses compared to ultrasound technology.

Figure 4:
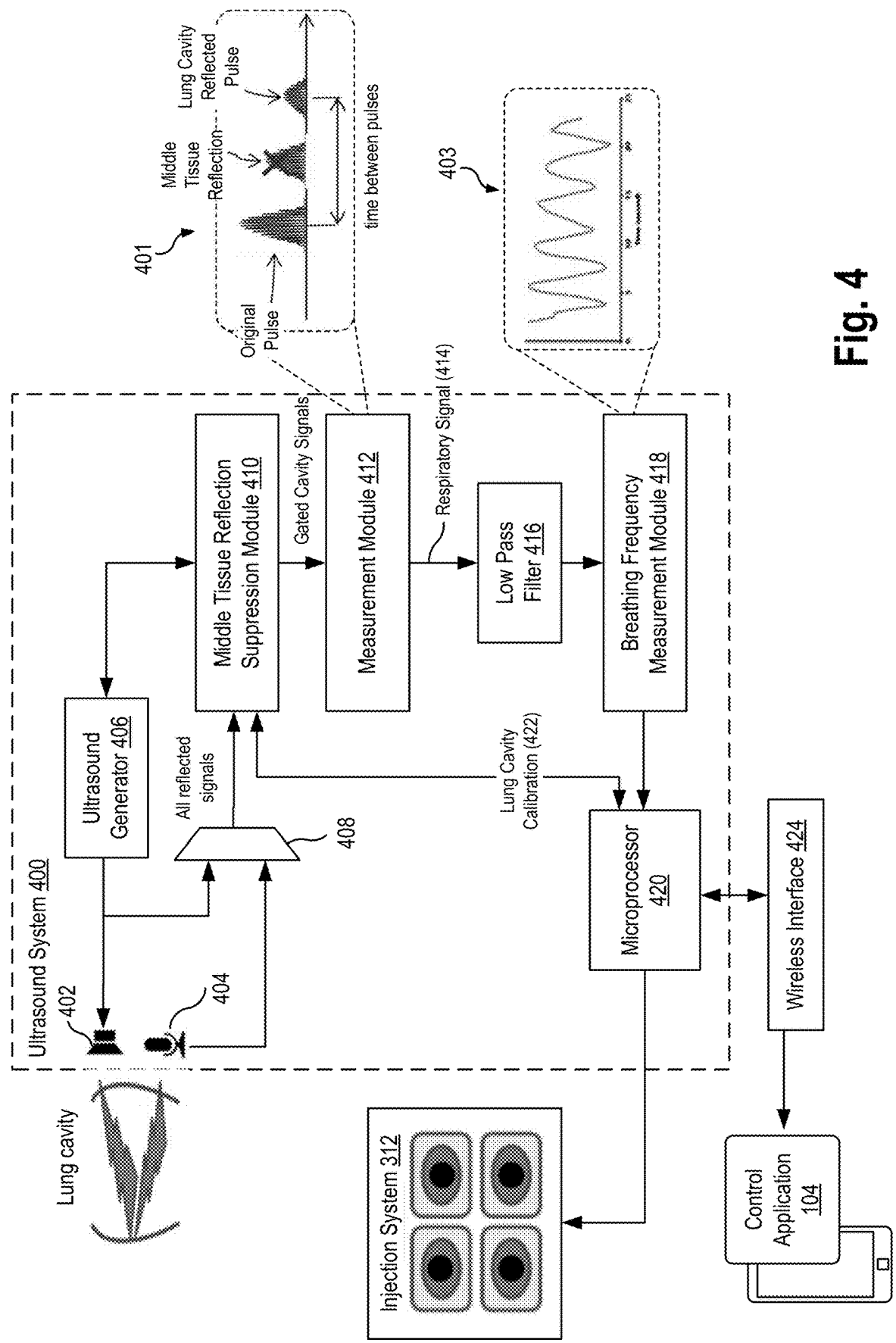
FIG. 4 is a schematic diagram of a respiratory rate sensor having an ultrasonic sensor system, according to an aspect of the present disclosure.

FIG. 4 is a schematic diagram of a respiratory rate sensor having an ultrasonic sensor system 400, according to an aspect of the present disclosure. The described system 400 employs a technique for using ultrasound signals to detect and monitor a user's respiratory rate. It has been determined that ultrasonic modulated pulses from ultrasound waves reflected by the lung cavity border in the human body are displaced by a time proportional to lung cavity size. The time calculated between pluses can be correlated with the size of the lungs at each measurement instant. In other words, the ultrasonic sensor system 400 is able to infer the respiratory rate based on the change in lung size (i.e., caused by respiration) as detected by ultrasound. To refine this measurement technique, the described system suppresses middle tissue reflection based on calibrated information about basic lung cavity size, as describe later.

As shown, the ultrasonic system 400 of the respiratory rate sensor includes an ultrasonic emitter 402, ultrasonic receiver 404, and an ultrasound generator 406. In some aspects, the ultrasonic emitter 402 and receiver 404 may be integrated into a single ultrasonic transceiver. The ultrasound generator 406 is configured to provide an electrical signal (transmitter signal) having a specified frequency and modulation to the ultrasonic emitter 402. The ultrasonic emitter 402 converts the electrical signal into ultrasound pulses that are directed to and transmitted through the lung cavity of the user. The ultrasonic receiver 404 is configured to receive ultrasonic signals (i.e., ultrasound which has reflected back through the user's body) and generate a resulting electrical signal based on the reflected ultrasound.

In one aspect, the ultrasonic system 400 may include a processing system having an adder element 408, a middle tissue suppression module 410, a measurement module 412, a low-pass filter 416, and a breathing frequency measurement module 418. The adder element 408 is configured to combine the resulting electrical signal receiver from the ultrasonic receiver 404 with the original transmitter signal into a combined signal that reflects all reflected signals, which is reflected in the waveform 401 depicted in FIG. 4.

The waveform 401 includes portions of the signal corresponding to the original pulse (i.e., transmitter signal), portions of the signal corresponding to the lung cavity reflected pulse, and some portions of the signal corresponding to ultrasound reflecting off unrelated "middle tissue" within the body. Accordingly, the middle tissue reflection suppression module 410 is configured to processes all reflected signals to obtain gated cavity reflection signals. In one implementation, the middle issue reflection suppression module 410 is configured to modify the combined signal to remove signals corresponding to middle tissue reflection based on lung cavity calibration information received from the microprocessor 420, as depicted in the waveform 401.

The measurement module 412 is configured to measure the distance between emitted and reflected pulses to produce an instant lung size. As mentioned earlier, it has been determined that ultrasound modulated pulses from ultrasound waves reflected by lung cavity border are displaced by a time proportional to lung cavity size. Time between pulses can be equal to or proportional to the size of the lungs at each measurement instant. As such, the measurement module 412 determines the time duration between the original pulses and the reflected ultrasound pulses based on the signal (which was modified by middle tissue suppression.)

In one aspect, the output of the measurement module 412 is a respiratory signal 414, which is then processed by a low pass filter 416 to suppress heartbeat-produced error, and finally by a breathing frequency measurement module 418. For example, each instant lung size measurement (by the measurement module 412) creates a respiratory waveform (signal 414) in the range of 12 to 20 times a minute in an average adult, as depicted by the waveform 403. The waveform 403 graphs the instant lung size over time (seconds). It has been determined that the human heartbeat can create a lung size error at the minimum frequency of 40 times a minute for an adult during sleep. Since heartbeat and respiratory frequency are demonstrably far apart, it has been determined that the heartbeat produced error can be easily filtered by a low pass filter, such as the filter 416 shown in FIG. 4.

The wearable device 106 may include a microprocessor 420 with an emergency trigger detector that activates drug injection when respiratory frequency is measured below a critical rate. That is, the microprocessor 420 may be configured to actuate the injector unit 312 to inject the medication into the body of the user in response to determining that the respiratory rate of the user is less than a threshold respiratory rate indicative of opioid overdose. In some aspects, the threshold respiratory rate may be a pre-determined static value (e.g., less than 12 breaths per minute). In other aspects, the threshold respiratory rate may be a dynamically determined value based on previously-measured respiratory rates of the user. In some aspects, the comparison with threshold respiratory rate may performed using a time-averaged value of the user's respiratory rate. In alternative embodiments, as mentioned earlier, the comparison with a threshold value may be based on whether the user's instant respiratory rate exceeds or is greater than a threshold value indicative of a medical condition related to increased respiration (e.g., hyperventilation, hypocapnia). In yet other embodiments, the threshold value(s) may be dynamically determined to define a range of "regular" or typical respiratory rates based on previously measured respiratory rates of the user, and the comparison with this threshold value(s) can be used to detect an "irregular" respiratory rate.

In some aspects, the processor 420 may be communicatively paired with a mobile device 102 executing a user control application 104 via a wireless interface 424 (e.g., Bluetooth, Wi-Fi interface). The processor 420 may provide indications to the user control application 104 of the current measured respiratory rate for monitoring or logging purposes, as well as indications of when certain conditions are triggered by the measured respiratory rate. For example, the processor 420 may provide the user control application 104 with an indication that the respiratory rate of the user has reached below the threshold rate and/or the injection action is imminent. In some aspects, in response to such an indication, the user control application can present an option to the user via a user interface to intervene in the injection of the medication. In other aspects, in response to receiving an indication that the measured respiratory rate of the user has reached a threshold rate, the user control application 104 transmit an alert message to a pre-determined list of contacts (e.g., via wireless connectivity) or place a telephone call to emergency or medical services (e.g., via cellular services).

FIG. 5 is a schematic diagram depicting operations of the microneedle injector system 500 according to one embodiment. FIG. 5 depicts different states of the injector system 500, including a state 501A prior to triggering the medicine injection, a state 501B during triggering the medicine injection, and a state 501C after triggering the medicine injection.

In one aspect, the injector system 500 may include a spring-loaded shaft 502, a pouch 504 containing the opioid overdose medication, a microneedle array 506, and an electromagnet 508 controlled by electronics (electronics 308). As shown in state 501A, a latch 510 retains the loaded spring of the shaft 502 from pushing against the pouch 504. In one aspect, the shaft 502 includes a distal element having dimensions suitable to evenly distribute pressure and force onto the pouch 504 when biased.

As shown in state 501B, upon triggering the injector, the latch 510 is actuated by the electromagnet 508, and the spring 503 is released. The spring 503 biases the shaft 502 towards the pouch 504 (releasing the medicine into the microneedle array) and biasing the microneedle array 506 into the user's skin, subsequently injecting the medicine into the user's skin (e.g., intradermally, transdermally, subcutaneously). After triggering the injector, the pouch remains empty, and the released medicine is inside the user's body. In some embodiments, the user may use a manual push button 512 to mechanically release the latch 510 and actuate the injector, thereby manually causing the injection of medicine. In some embodiments, the user may use the manual push button to retrieve the MN array 506 from the body and rewind the release spring 503.

Figure 6:
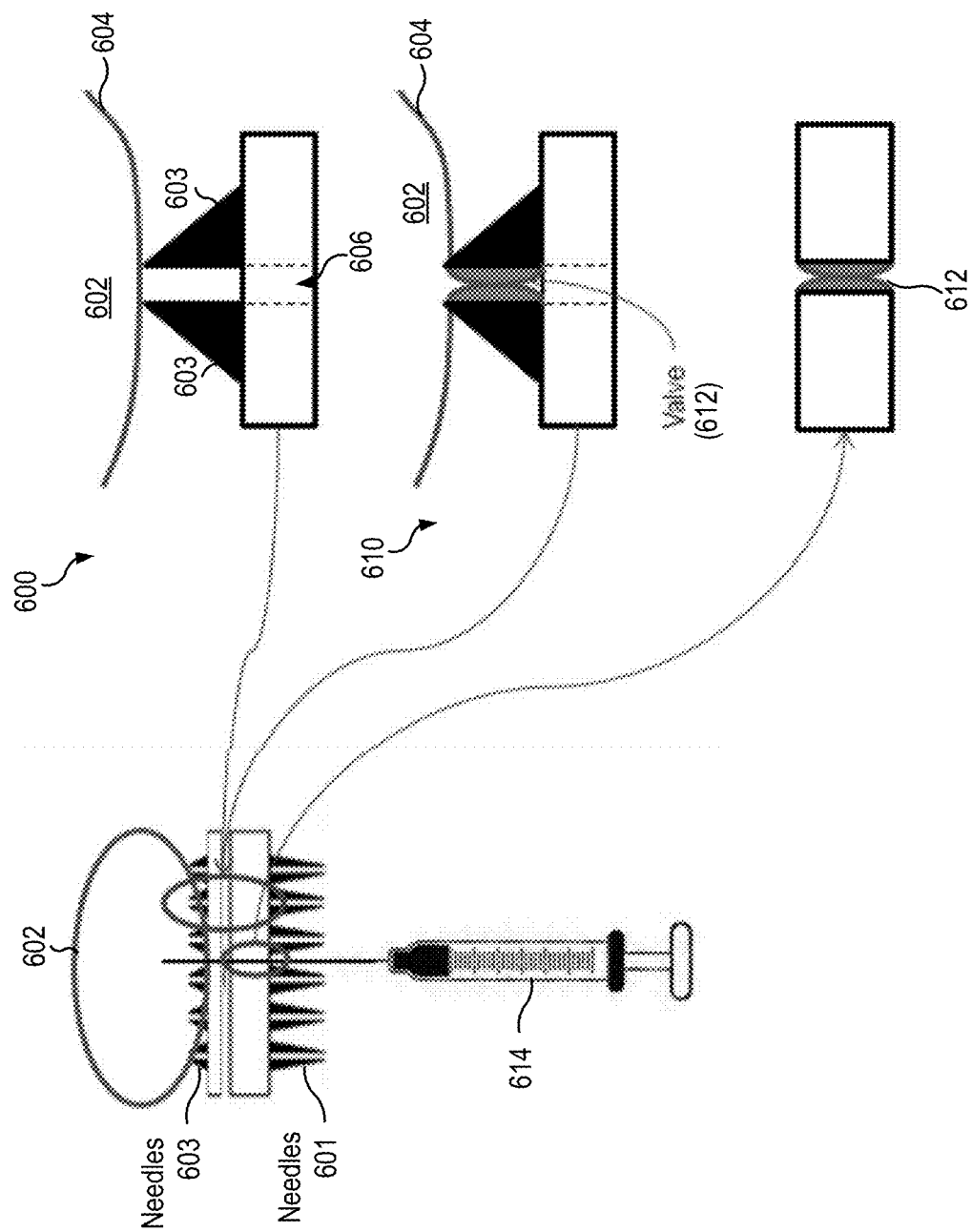
FIG. 6 depicts various embodiments of an assembly of a pouch and microneedle array in greater detail.

FIG. 6 depicts various embodiments of an assembly of a pouch and microneedle array in greater detail. In one embodiment, the injector unit may include a microneedle (MN) array unit 600 that is a single-use device that is replaceable after each use, i.e., after administration of a dosage of medication. In such embodiments, during injection, an actuator (e.g., shaft 502) pressing a pouch 602 causes sharp needle edges 603 to puncture a membrane 604 of the pouch to open a flow of medication. The flow of medication travels through a path 606 defined through the opening created by the needles 603 and through the microneedle array 601. To replace this single-use unit, a replacement procedure may be performed that includes rewinding the spring of the injector unit, removing the used MN array, and installing a new MN array module with a full medicine pouch 602. In some embodiments, the MN array module is configured to use a replaceable pouch, in which case, only the medicine pouch needs to be replaced.

In another embodiment, the injector unit may include a MN array unit 610 of a permanent design, for example, having a permanent pouch and microneedle array that is configured to be refilled after use(s). In such embodiments, the pouch and MN array unit are an integrated unit such that a membrane of the pouch is sealingly coupled to a valve 612 of the MN array unit 610. During injection, the medicine under pressure from the actuated shaft causes the valve 612 to open and begin the medicine flow. Afterwards, the pouch could be refilled with medicine using a syringe-type device 614. For example, a syringe system can be used in the manufacturing process to remove air and replace the pouch with medicine or with an embodiment that has a permanent microneedle and pouch system. The valve 612 of the MN array unit may be formed from a material (e.g., soft plastic) that is flexible enough to allow a syringe needle to penetrate (for refilling) yet rigid enough to keep medicine from leaking from the pouch.

FIG. 7 depicts a medicine release and pullback shaft electric motor based system 700 configured as a permanent injection system according to one embodiment. Instead of using a spring-loaded shaft as seen in FIG. 5, the microneedle injector unit 700 may include a shaft and electric-motor-based system for medicine release and pullback. In such an embodiment, the microneedle injector unit 700 may include an electric motor 702, a rotating unit 704 coupled to the motor (e.g., a rotating nut), a threaded shaft 706 coupled to the rotating unit, and a microneedle array 712. The microneedle injector unit 700 may further include a reservoir 714 containing liquid medicine 716 for treating opioid overdose symptoms.

In one embodiment, a microprocessor of the wearable device 106 may rotate the injector motor 702 to achieve two steps: first, to move the MN array 712 into the user's skin, and second, to produce shaft motion sufficient to dispense one dose of the medicine 716. In some aspects, the motor 702 causes (via the rotating unit 704) the shaft 706 to move in a linear "downwards" direction towards the skin 722. The shaft motion may cause a plunger 720 to change a volume 718 of the reservoir 714 and cause the medicine outflow through the MN array 712. The shaft motion further cases the MN array 712 to be pressed against the user's skin, subsequently injecting the medicine into the user's skin transdermally and/or intradermally. After the medicine 716 has been dispensed, the motor 702 may rotate in the opposite direction, allowing the MN array 712 to pull out from the body (an "upwards" motion). Valves in the microneedle array 712 and base will prevent the air to be sucked in and will create an upward pressure to withdraw the MN array 712 from the body. As shown, a syringe 730 can be used to fill up the medicine 716 in coordination with the motor moving the shaft upwards.

FIG. 8 depicts an alternative embodiment of the permanent injection system configured to perform medicine release and pullback using a dual electric motor based system 800. As shown, the injector unit 800 may include two subsystems having separate electric motors: an injection needle motor 802 and a medicine dispense motor 812. The first subsystem having the injection needle motor 802 may include a corresponding rotating unit 804 and threaded shaft 806 coupled to an injection needle 808. The second subsystem having the medicine dispense motor 812 may include another rotating unit 814 and a threaded shaft 816 that is coupled to a reservoir 818. In the aspect shown, the injector subsystem and the medicine subsystem may be coupled to an injection unit base 822. The injector subsystem and the medicine subsystem may be fluidly coupled by a flexible tubing 805, which permits medicine 817 to reach the injection needle assembly.

During injection, the microprocessor of the electronics 308 engages the two injection motors 802, 812 to achieve two steps: first, to insert the injection needle 808 into the skin 820; and second, to engage the shaft motion just enough to dispense one dose of medicine 817. After injection, by rotating in an opposite direction, the injection needle motor will pull the injection needle out from the body when the medicine is dispensed. A refilling syringe 830 can be used to fill-up the medicine reservoir 818 in coordination with the motor moving the threaded shaft 816 "upward" or away from the reservoir.

Bracelet Method Using Photoplethysmographic (PPG) Sensing

In another embodiment of the present disclosure, the wearable device may be configured to detect opioid overdose of the device wearer using photoplethysmographic (PPG) sensing (i.e., instead of or in addition to the ultrasonic sensing embodiment described above). A PPG signal can carry two signal components: heart rate and respiratory signal. It has been determined that the heart rate signal component and the respiratory signal components are displaced in frequencies. For example, the heart rate may have a frequency between 45 Hz to 160 Hz, and the respiratory signal may be between 6 Hz to 15 Hz. A PPG signal acquisition and processing system may extract the respiratory signal using a variety of techniques, such as a wavelet decomposition technique or other suitable frequency transform decomposition technique that allows extraction of respiratory frequency component. As such, the wearable device may be configured to determine a respiratory rate of the device wearer based on the oxygen saturation of the wearer's blood. In another aspect, the wearable device may be configured to determine a heart rate of the device wearer using PPG sensing.

Figure 9:
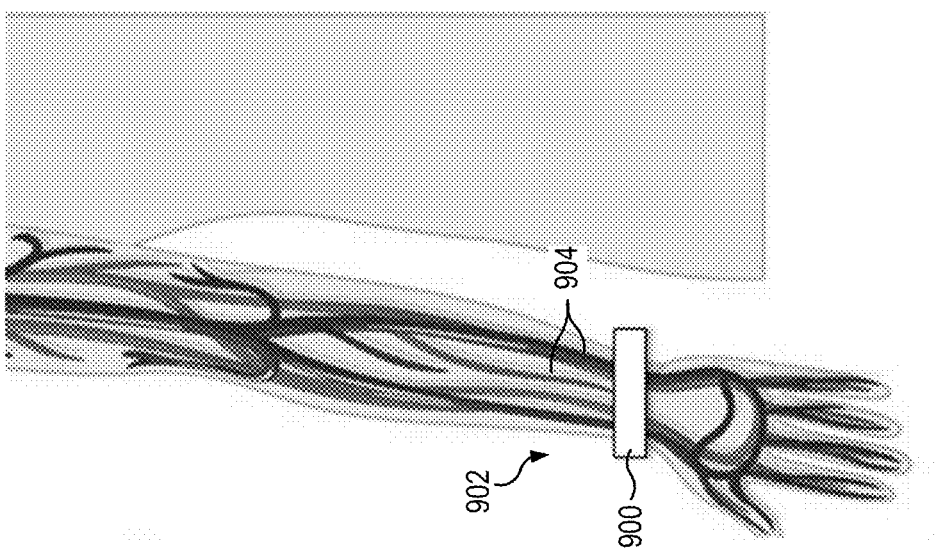
FIG. 9 is a block diagram depicting one embodiment of a wearable device configured to use photoplethysmogram (PPG) based sensing techniques.

FIG. 9 is a block diagram depicting one embodiment of a wearable device 900 configured to use photoplethysmogram-based sensing techniques. The user may wear the wearable device 900 on a location of their body suitable for optically obtaining a photoplethysmogram on a portion of the user's skin surface. For example, the wearable device may be in the form of a bracelet or bracelet-like device (e.g., smart watch) worn around a wrist 902 of the user. In another example, the wearable device 900 may be secured to the user's body via adhesive, such as tape, or by other fastening means, such as a belt. The wearable device may be configured to determine health metrics (e.g., a respiratory rate) of the device wearer based on the oxygen saturation of the wearer's blood.

Figure 10:
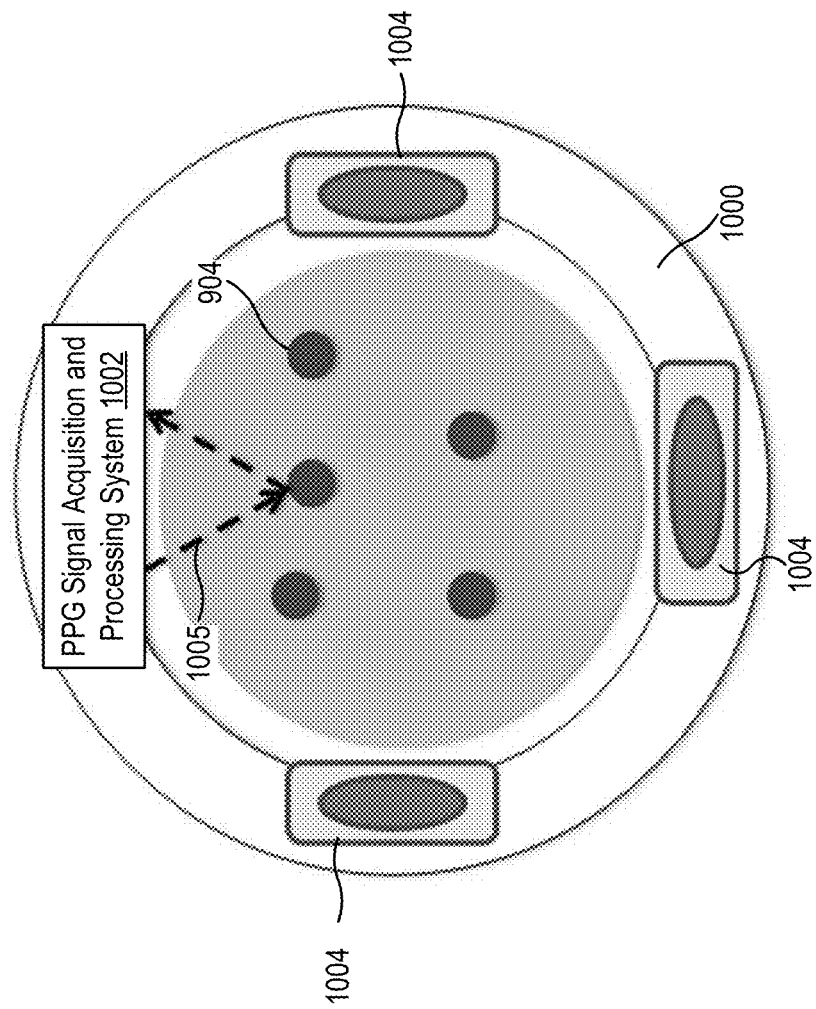
FIG. 10 is a block diagram illustrating a cross-sectional view of an example PPG sensor and drug injector bracelet.

FIG. 10 is a block diagram illustrating a cross-sectional view of an example PPG sensor and drug injector bracelet 1000. The PPG sensing and drug injecting bracelet 1000 may include a photoplethysmographic signal acquisition and processing system 1002, a wireless rechargeable battery that powers the device, various electronics including a wireless modem (e.g., Bluetooth or Wi-Fi), and one or more medicine injection modules 1004. The PPG sensing and drug injecting bracelet may include a pulse oximeter that indirectly monitors the oxygen saturation of the wearer's blood and changes in the blood volume in the skin proximate to the wearable device. In one implementation, the photoplethysmographic signal acquisition and processing system 1002 may be perform PPG sensing using IR light 1005 generated and reflected by blood vessels 904 in the skin of the wearer. The medicine injection modules 1004 may be similar to the medicine injection modules described in conjunction with the ultrasound-based embodiment, e.g., microneedle arrays, microneedle capsules with actuators (e.g., spring, motor), injectors using one-time use capsules or refillable pouches.

Figure 11:
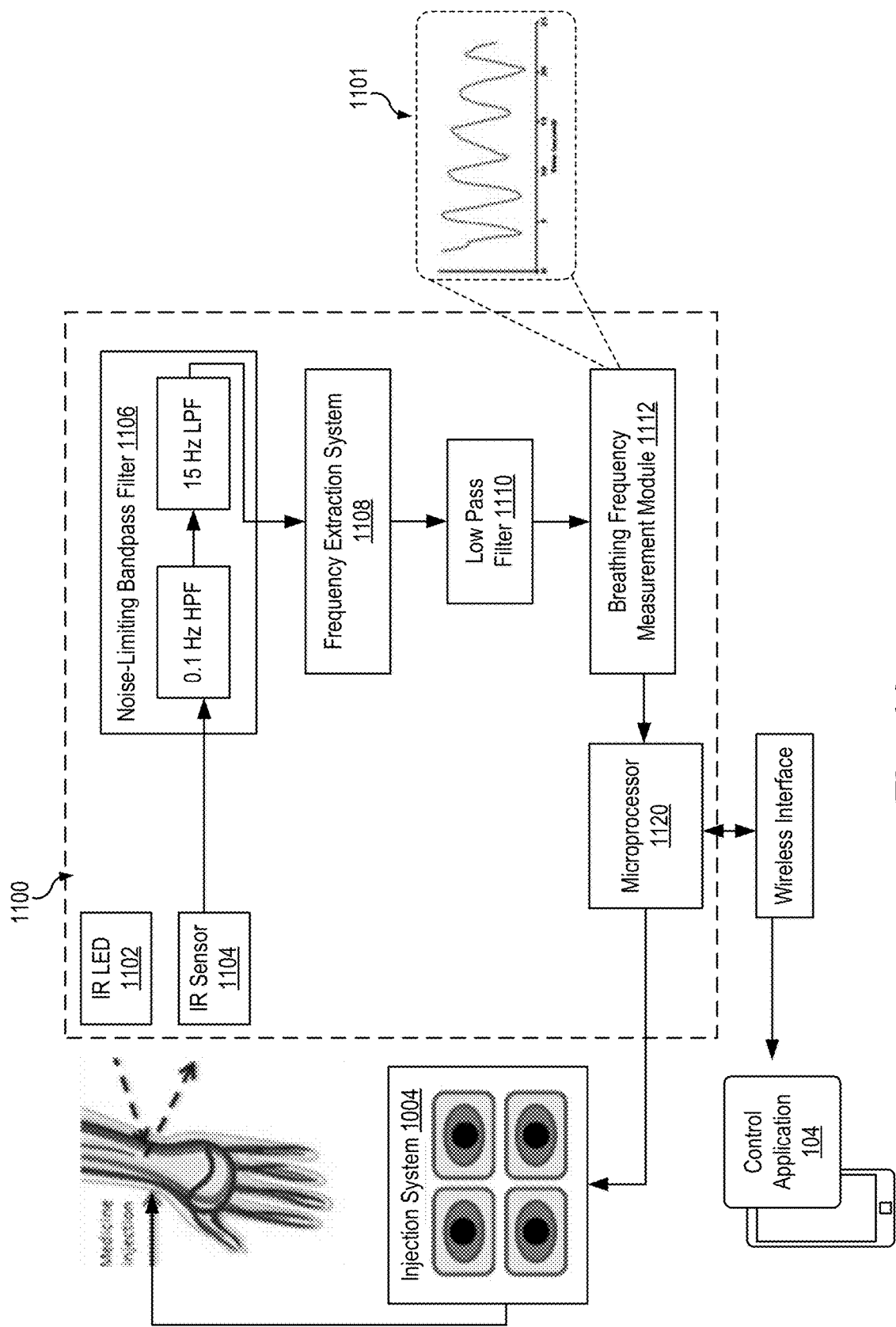
FIG. 11 is a schematic diagram of a respiratory rate sensor having a photoplethysmographic signal acquisition and processing system according to one embodiment.

FIG. 11 is a schematic diagram of a respiratory rate sensor having a photoplethysmographic signal acquisition and processing system 1100 according to one embodiment. As shown, the photoplethysmographic signal acquisition and processing system 1100 may include one or more light-emitting sources 1102 (e.g., infrared light-emitting diodes, or IR LEDs) configured to generate IR light directed at the skin of the user, and one or more light sensors 1104 or photodiodes (e.g., IR sensor) configured to detect the light reflected by blood vessels in the user's skin and generate a resulting output signal. The output signal from the IR sensor may be a physiological waveform which is associated with the (small) variations in the reflected IR light caused by the varying blood volume in the tissue proximate to the bracelet (e.g., tissue near the wrist). As such, the output signal (waveform) may be considered synchronous with the pulse of the device wearer.

In one aspect, the PPG signal acquisition and processing system 1100 may include a processing system having a noise-limiting bandpass filter (BPF) 1106 configured to allow signals within a selected range of frequencies (such as using a 0.1 Hz high-pass filter and a 15 Hz low-pass filter, although other specific frequencies may be used). The PPG signal acquisition and processing system 1108 also includes a frequency extraction module 1108 configured to perform DWT (discrete wavelet transform) wavelet decomposition or other DSP (digital signal processing) extraction on the resulting signal from the BPF to extract portions of the signal pertaining to a respiratory signal. In some aspects, the frequency extraction module 1108 may be configured to use other suitable frequency transform decomposition techniques that allows extraction of respiratory frequency component from the input signal. This signal may be further processed by a low pass filter 1110 configured to suppress heartbeat-produced error (similar to the low pass filter shown in FIG. 4), and finally by a measurement module 1112. The measurement module 1112 is configured to generate a respiratory signal (as depicted by the waveform 1101)

The wearable device 1000 may include a microprocessor 1120 with an emergency trigger detector that activates drug injection (by the medicine injection system) in response to determining that the respiratory frequency is below a critical threshold rate. Similar to the microprocessor shown in FIG. 4, the microprocessor 1120 may be configured to actuate the injector unit 1004 and cause the opioid overdose medication to be injected into the body of the user upon detecting the respiratory rate of the user has reached a critical respiratory rate that is indicative of opioid overdose.

Figure 12:
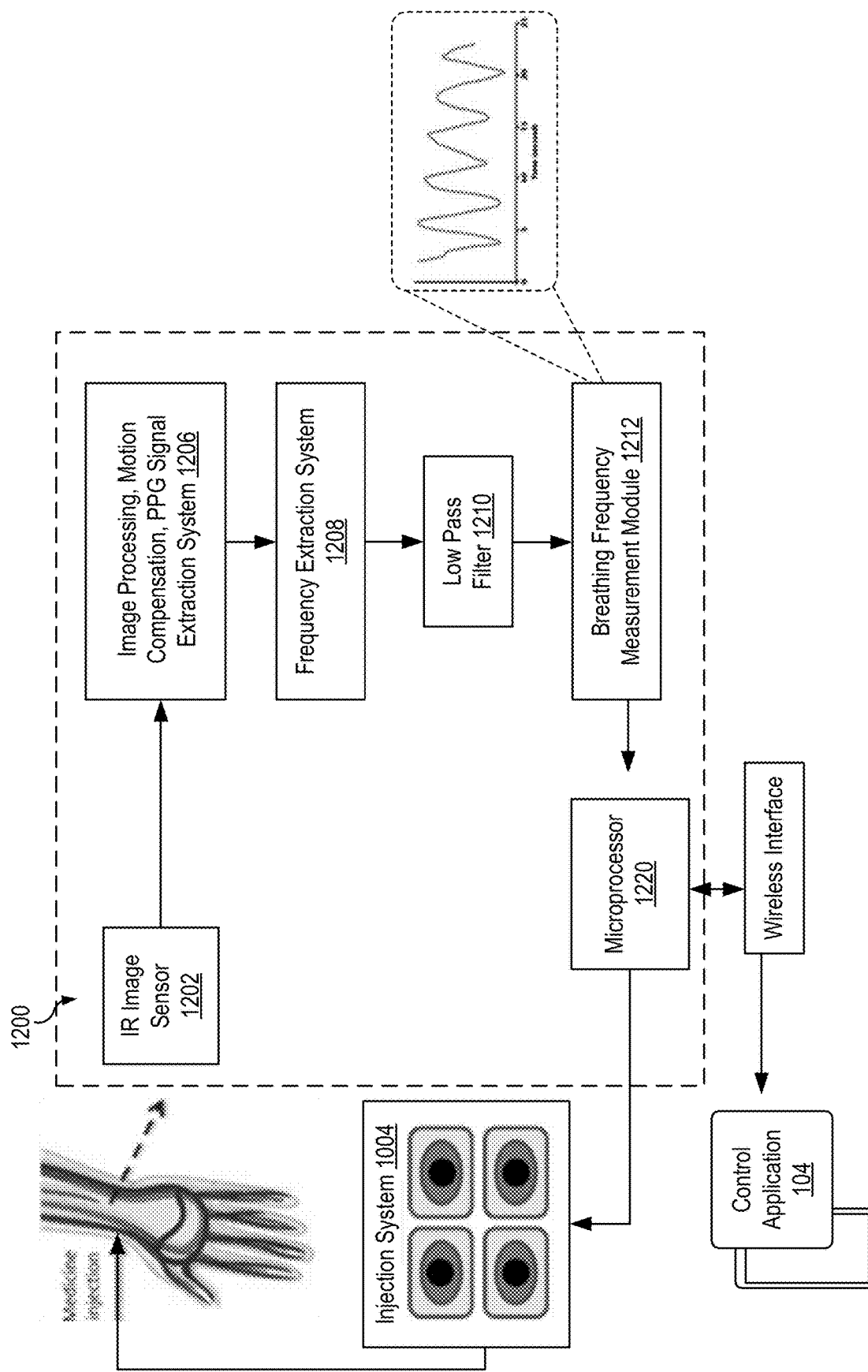
FIG. 12 is a schematic diagram of a respiratory rate sensor having a photoplethysmographic signal acquisition and processing system according to an alternative embodiment that uses image processing.

FIG. 12 is a schematic diagram of a respiratory rate sensor having a photoplethysmographic signal acquisition and processing system 1200 according to an alternative embodiment that uses image processing. As shown, the photoplethysmographic signal acquisition and processing system 1200 may include one or more image sensors 1202 (e.g., IR image sensors) configured to generate image data of a portion of the user's body using infrared radiation. The image sensor 1202 may be a thermographic camera, infrared camera, thermal imaging camera, or other type of optical device configured to record image data (e.g., single images, or sequence of images) and/or video data. In one aspect, the IR image sensor 1202 may be configured to generate a sequence of images of the blood vessels in the user's skin.

Figure 13:
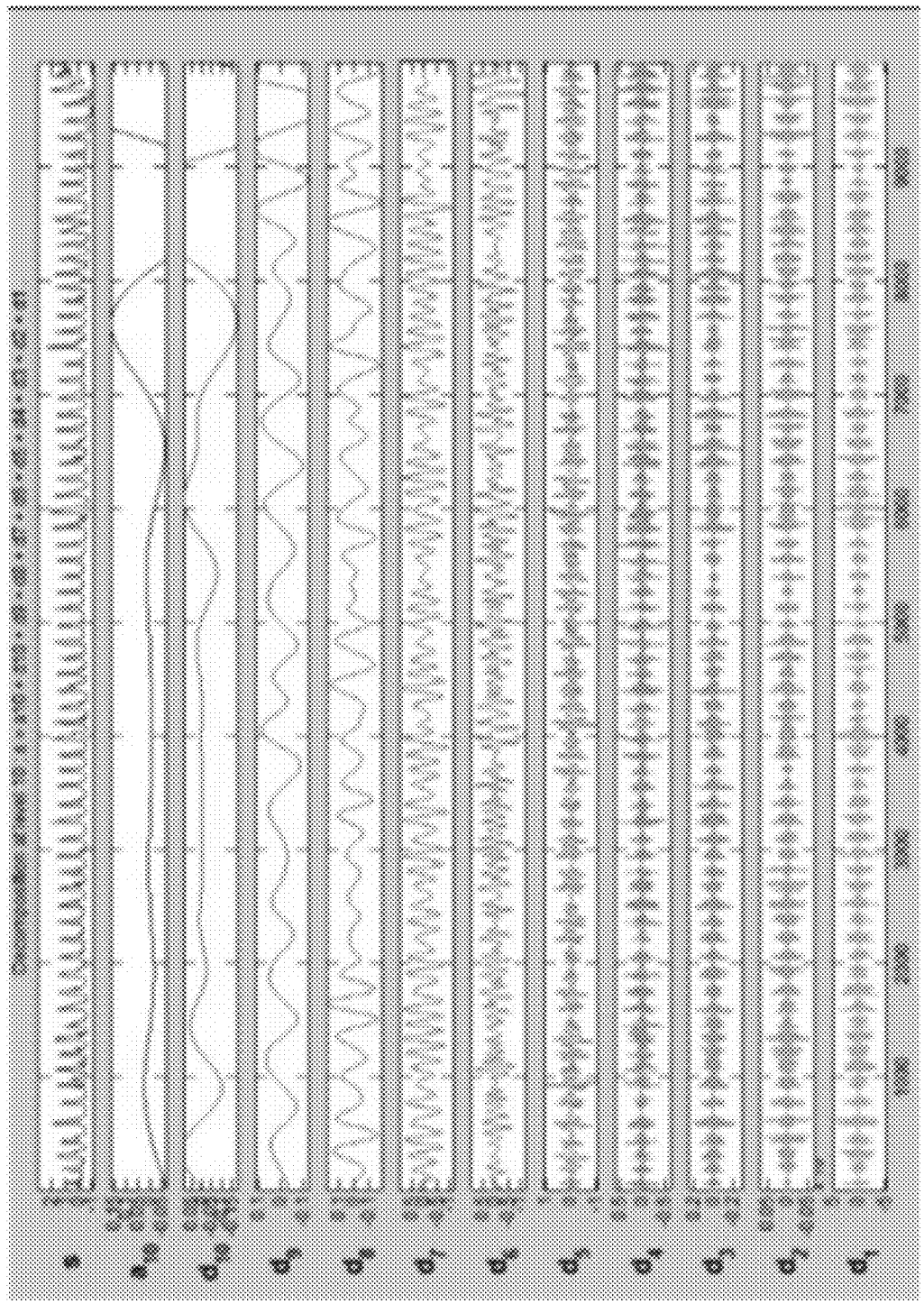
FIG. 13 illustrates various waveforms resulting from example wavelet decomposition as performed by the photoplethysmographic signal acquisition and processing system.

According to an aspect, the PPG signal acquisition and processing system 1200 is configured to detect slight variations within the sequence of images of the blood vessels that correspond to changes in volume of the blood vessels during a pressure pulse (e.g., which distend the arteries and arterioles in the subcutaneous tissue). The PPG signal acquisition module 1200 may include an image processing system 1206 configured to perform image processing, motion compensation, and PPG signal extraction on the image data provided by the IR image sensor. The described system may perform image processing on the image and generate a resulting output PPG signal. The resulting output signal may be further processed similarly to the embodiments described above, e.g., a frequency extraction module 1208, a low pass filter 1210, a measurement module 1212, and a microprocessor 1220 having an emergency trigger detector that activates drug injection (by the medicine injection system 1004) in response to determining that the respiratory frequency (which was determined based on IR image processing) is below a critical threshold rate FIG. 13 illustrates various waveforms resulting from example wavelet decomposition as performed by the photoplethysmographic signal acquisition and processing system. One-dimensional (1-D) wavelet decomposition signal processing method can be used for the further processing of the original resulting signal (e.g., from the IR sensor). The waveform "S" seen at the top of FIG. 13 represents the original PPG signal. In one approach, the PPG waveform (S) comprises a physiological waveform attributed to cardiac synchronous changes in the blood volume with each heartbeat, and can be superimposed on a slowly varying baseline with various lower frequency components attributed to respiration, nervous system activity, and thermoregulation. FIG. 13 further illustrates the wavelet decomposition of the waveform S at a range of levels (i.e., a10, d10 to d1). The level of decomposition may be selected based on the frequency of a respiratory signal (e.g., 6 Hz to 15 Hz) which has to be extracted from the original PPG signal. As shown, the waveforms labeled D1 to a10 represent a range of 1-D wavelet decomposition coefficients that were decomposed using wavelet decomposition. It has been determined that the waveform generated using the D9 coefficient represents a respiratory signal with a high level of accuracy between 71% and 93%.

Additionally, aspects of the present disclosure may be extended to use other techniques for determining the respiratory rate of a user. For example, the sensor may be configured to use impedance phlebography, or impedance plethysmography (IPG), which measures small changes in electrical resistance of the user's body that reflect blood volume changes. In this example, the sensor may include at least a pair of electrodes conductively coupled to the body of the user: a first electrode for applying a current to a region of the user's body, and a second electrode for receiving a resulting voltage signal. The resulting signal may be electronically processed to extract signal features, which is used to determine a respiratory rate of the user. In another example, the sensor may be configured to perform airflow breath detection to determine the respiratory rate of the user.

Figure 14A:
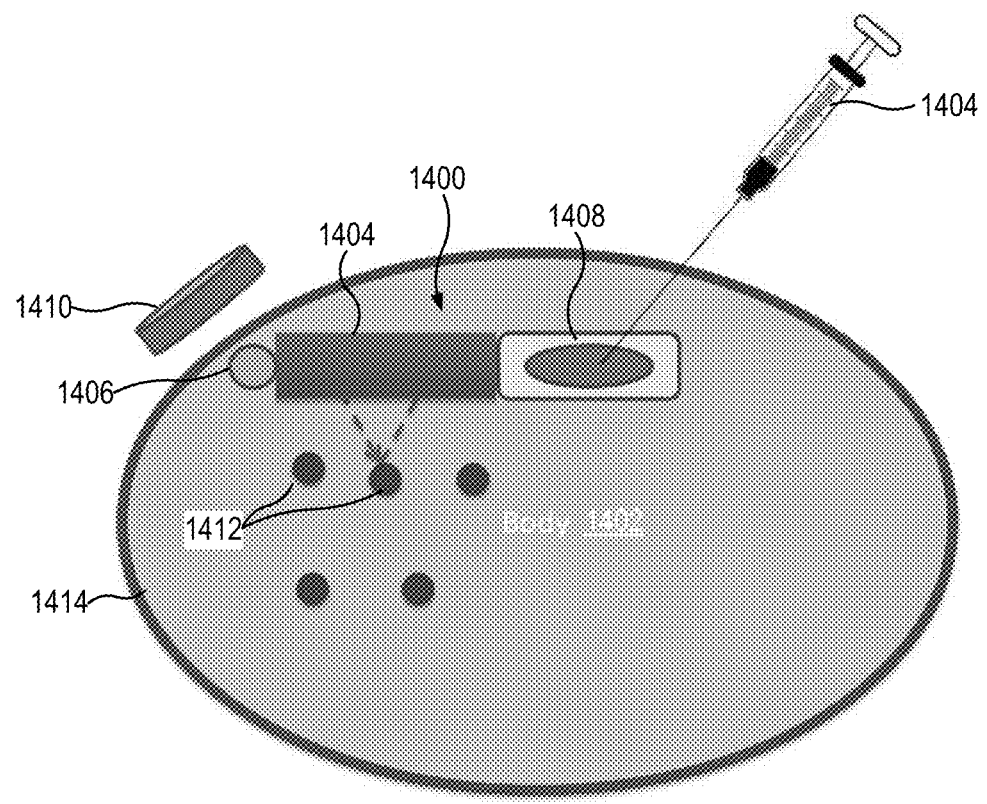

FIGS. 14A and 14B are block diagrams of a medical device 1400 according to one aspect of the present disclosure. The medical device 1400 may be configured similar to the wearable bracelet 1000 described above, except the medical device 1400 is configured as an embedded module. The embedded module 1400 may be configured to use the photoplethysmogram-based sensing techniques (or the sonar-based techniques) to detect opioid overdose and release anti-overdose medicine inside of the user's body. The embedded module 1400 may be implanted within a user's body 1402 through a surgical procedure. The user may have the embedded module 1400 inserted in a location of their body suitable for optically obtaining a photoplethysmogram from blood vessels 1412 within the user's body 1402 (e.g., in the user's arm). In one aspect, the embedded module is configured with a size and shape for being inserted and disposed at a location within the user's body near blood vessels of soft tissue or near a artery or vein to have a clear PPG signal. The embedded module is configured to shine the optical device (e.g., laser, IR light) through the blood flow of the blood vessel, artery, or vein.

In one aspect, the embedded module 1400 may be a microchip implant configured to store one or more doses of anti-opioid overdose medication and selectively release such medication into the body of the user (without using needles or microneedle arrays) in response to detecting a critical respiratory rate.

The embedded module 1400 may be configured to determine health metrics (e.g., a respiratory rate) of the device wearer based on the oxygen saturation of the user's blood. In one aspect, the embedded module 1400 may include a photoplethysmographic signal acquisition and processing system 1404, a wireless rechargeable battery 1406 that powers the device, various electronics including a wireless modem (e.g., Bluetooth or Wi-Fi), and one or more medicine release units 1408. The PPG signal acquisition and processing system 1404 may include a pulse oximeter that indirectly monitors the oxygen saturation of the wearer's blood and changes in the blood volume in the skin proximate to the wearable device. In one implementation, the PPG signal acquisition and processing system 1404 may perform PPG sensing by generating IR light that is reflected by blood vessels 1412 within the body 1402 of the user. The rechargeable battery 1406 may be configured to be charged using inductive charging, for example, by a corresponding charging station 1410 that creates an alternating electromagnetic field that permeates skin (1414) of the user and reaches the rechargeable battery 1406.

In some aspects, the medicine release units 1408 may be similar to the medicine injection modules described above (e.g., using one-time use capsules or refillable pouches) except they may release the medicine without the use of needles or microneedle arrays. That is, rather than penetrating the skin to discharge medicine under the skin (as in the case of a microneedle or needle array), the medicine release units 1408 is surgically implanted under the skin so that no skin-penetrating needles are needed. The medicine release unit may use valves (e.g., valves 1422) to discharge medicine inside the body. As shown in FIG. 14B, the valve 1422 is a valve that will release medicine under pressure from the piston 1424 driven by the motor 1421. The valve 1420 can be used to replenish medicine from a syringe 1404. The action of the syringe is configured to be synchronous with a reverse action of the piston 1424 and motor 1421.

The medicine release unit(s) 1408 may further include one or more base valves 1422 for medicine release that are disposed in apertures of the units 1408 and are configured to fluidly transmit the opioid medicine into the body through the apertures. In one implementation, the medicine release units 1408 may include a motorized mechanism similar to that described in conjunction with FIG. 7, in which a motor is actuated to apply sufficient pressure to a volume of opioid medicine 1424 to cause the base valves 1422 to open and permit a dosage of medicine 1424 to release into the body of the user.

In some aspects, the medicine release units 1408 may be configured to be refilled by, for example, a syringe 1404. As shown in FIG. 14B, the medicine release units 1408 may include a base valve 1420 for medicine injection that is configured to sealingly receive a refilling syringe 1404 that contains the overdose medicine. The syringe 1404 may be used to initially fill the medicine release unit 1408 (such as during a manufacturing process) or refill the medicine release unit 1408 while the embedded module 1400 is disposed within the user's body. In some aspects, the valve 1420 of the medicine release unit 1408 may be formed from a soft plastic material that will allow medicine to be injected into the medicine release.

In one aspect, a special passive syringe 1430 can be used to make this operation of replenishment easier. The passive syringe 1430 may include an elastic container having an internal volume filled with the opioid overdose medicine, such as a soft rubber balloon 1432 with medicine. The passive syringe 1430 is configured to empty itself out in response to a "sucking" reverse action of the piston 1424 driven by the motor 1421. This passive syringe 1430 may be configured as a disposable one-time use article or a reusable multiple-use device. In aspects in which the passive syringe 1430 is a multiple use device, the passive syringe can be replenished externally to the body by sucking in medicine in the reverse vacuum expansion of the rubber balloon 1432.

Figure 15:
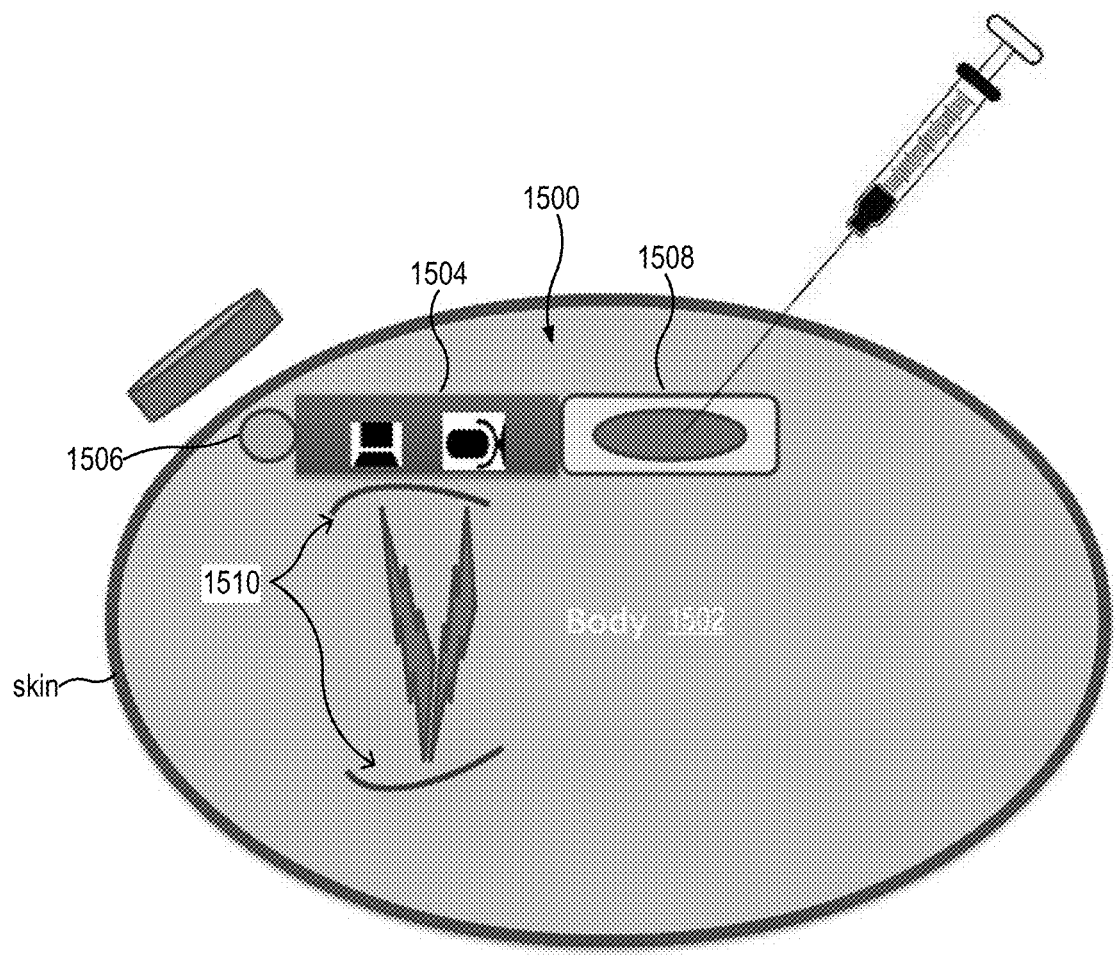
FIG. 15 is a block diagram of a medical device for ultrasound-based opioid overdose sensing according to one aspect of the present disclosure.

FIG. 15 is a block diagram of a medical device 1500 for ultrasound-based opioid overdose sensing according to one aspect of the present disclosure. The medical device 1500 may be similar to the wearable device 106 described above except the medical device is configured as an embedded module 1500, e.g., implantable within a user's body 1502 through a surgical procedure. The user may have the embedded module 1500 inserted in a location of their body, such as the torso or the side ribcage of the user's body 1502, suitable for transmitting to and reflecting ultrasonic waves (i.e., ultrasound) off to at least one lung cavity 1510 of the user's lungs. In one aspect, the embedded module 1500 may be configured with a shape suitable for being inserted and retained in a location near a lung cavity of the user, on top of or slightly below the ribs in front (anterior) or in the back (posterior) of the user's body. The embedded module 1500 is configured to send ultrasound sonar signals through the lung and sense any reflected signals from the lung cavity's internal tissue. The ultrasound signals are selected with a wavelength and frequency so as to sufficiently penetrate the user's ribs on the way from and on the way back to the sonar. The processor inside the embedded module registers a detected change of lung cavity size and derive the corresponding respiration rate.

The embedded module 1500 may be a microchip implant configured to store one or more doses of anti-opioid overdose medication and selectively release such medication into the body of the user (without using needles or microneedle arrays) in response to detecting a critical respiratory rate using sonar-based sensing techniques. The embedded module 1500 may be configured to measure a respiratory rate of the device wearer based on the changes in the ultrasound waves reflected through the lung cavity of the user. In one aspect, the embedded module 1400 may include a sonar signal generation and acquisition processing system 1504 (similar to the ultrasound system 400 described above), a wireless rechargeable battery 1506 that powers the device, various electronics including a wireless modem, and one or more medicine release units 1508.

While the embedded modules are herein depicted as integral units containing sensing, processing, and medicine release sub-systems, it is understood that aspects of the present disclosure include configurations in which the medical device is a combination of wearable and embedded subsystems. For example, a medical device may include a PPG-based sensing and processing system that is coupled to the skin surface of the user and that is communicatively coupled (e.g., via wireless communication) to a medicine release module embedded within the body of the user. In another example, a medical device may include an ultrasound-based sensing and processing system that is embedded within the torso of the user, for improved ultrasound transmission and detection, and that is communicatively coupled to a medicine injection system with a microneedle array that is coupled to the skin of the user.

Figure 16:
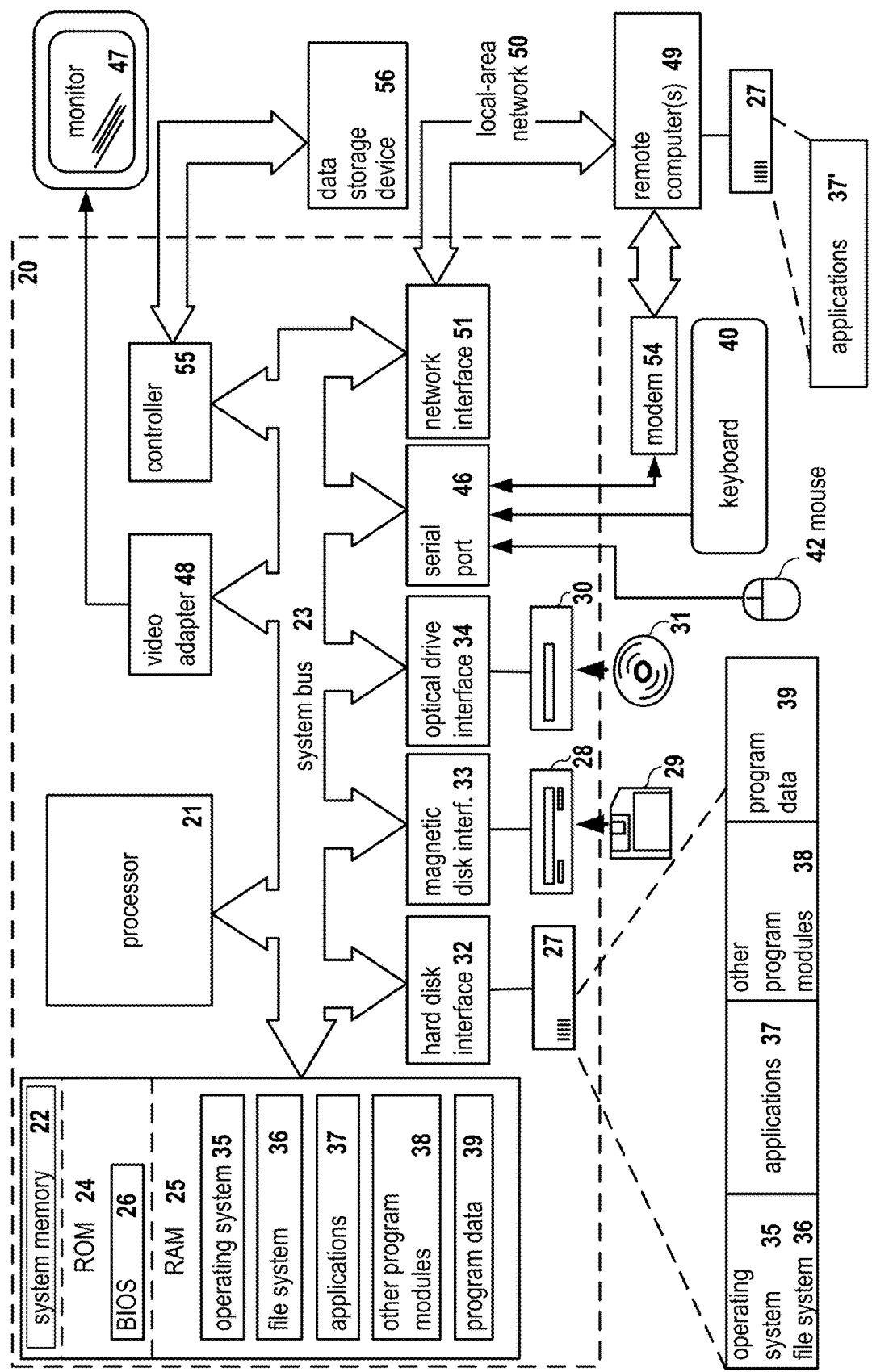
FIG. 16 is a block diagram of a computer system on which the disclosed system and method can be implemented according to an exemplary aspect.

FIG. 16 is a block diagram illustrating a computer system 20 on which aspects of systems and methods for treating opioid overdose using a wearable device may be implemented in accordance with an exemplary aspect. It should be noted that the computer system 20 can correspond to the control device 102, for example, described earlier.

As shown, the computer system 20 (which may be a personal computer or a server) includes a central processing unit 21, a system memory 22, and a system bus 23 connecting the various system components, including the memory associated with the central processing unit 21. As will be appreciated by those of ordinary skill in the art, the system bus 23 may comprise a bus memory or bus memory controller, a peripheral bus, and a local bus that is able to interact with any other bus architecture. The system memory may include permanent memory (ROM) 24 and random-access memory (RAM) 25. The basic input/output system (BIOS) 26 may store the basic procedures for transfer of information between elements of the computer system 20, such as those at the time of loading the operating system with the use of the ROM 24.

The computer system 20 may also comprise a hard disk 27 for reading and writing data, a magnetic disk drive 28 for reading and writing on removable magnetic disks 29, and an optical drive 30 for reading and writing removable optical disks 31, such as CD-ROM, DVD-ROM and other optical media. The hard disk 27, the magnetic disk drive 28, and the optical drive 30 are connected to the system bus 23 across the hard disk interface 32, the magnetic disk interface 33, and the optical drive interface 34, respectively. The drives and the corresponding computer information media are power-independent modules for storage of computer instructions, data structures, program modules, and other data of the computer system 20.

An exemplary aspect comprises a system that uses a hard disk 27, a removable magnetic disk 29 and a removable optical disk 31 connected to the system bus 23 via the controller 55. It will be understood by those of ordinary skill in the art that any type of media 56 that is able to store data in a form readable by a computer (solid state drives, flash memory cards, digital disks, random-access memory (RAM) and so on) may also be utilized.

The computer system 20 has a file system 36, in which the operating system 35 may be stored, as well as additional program applications 37, other program modules 38, and program data 39. A user of the computer system 20 may enter commands and information using keyboard 40, mouse 42, or any other input device known to those of ordinary skill in the art, such as, but not limited to, a microphone, joystick, game controller, scanner, etc. Such input devices typically plug into the computer system 20 through a serial port 46, which in turn is connected to the system bus, but those of ordinary skill in the art will appreciate that input devices may be also be connected in other ways, such as, without limitation, via a parallel port, a game port, or a universal serial bus (USB). A monitor 47 or other type of display device may also be connected to the system bus 23 across an interface, such as a video adapter 48. In addition to the monitor 47, the personal computer may be equipped with other peripheral output devices (not shown), such as loudspeakers, a printer, etc.

Computer system 20 may operate in a network environment, using a network connection to one or more remote computers 49. The remote computer (or computers) 49 may be local computer workstations or servers comprising most or all of the aforementioned elements in describing the nature of a computer system 20. Other devices may also be present in the computer network, such as, but not limited to, routers, network stations, peer devices or other network nodes.

Network connections can form a local-area computer network (LAN) 50 and a wide-area computer network (WAN). Such networks are used in corporate computer networks and internal company networks, and they generally have access to the Internet. In LAN or WAN networks, the personal computer 20 is connected to the local-area network 50 across a network adapter or network interface 51. When networks are used, the computer system 20 may employ a modem 54 or other modules well known to those of ordinary skill in the art that enable communications with a wide-area computer network such as the Internet. The modem 54, which may be an internal or external device, may be connected to the system bus 23 by a serial port 46. It will be appreciated by those of ordinary skill in the art that said network connections are non-limiting examples of numerous well-understood ways of establishing a connection by one computer to another using communication modules.

In various aspects, the systems and methods described herein may be implemented in hardware, software, firmware, or any combination thereof. If implemented in software, the methods may be stored as one or more instructions or code on a non-transitory computer-readable medium. Computer-readable medium includes data storage. By way of example, and not limitation, such computer-readable medium can comprise RAM, ROM, EEPROM, CD-ROM, Flash memory or other types of electric, magnetic, or optical storage medium, or any other medium that can be used to carry or store desired program code in the form of instructions or data structures and that can be accessed by a processor of a general purpose computer.

In various aspects, the systems and methods described in the present disclosure can be addressed in terms of modules. The term "module" as used herein refers to a real-world device, component, or arrangement of components implemented using hardware, such as by an application specific integrated circuit (ASIC) or field-programmable gate array (FPGA), for example, or as a combination of hardware and software, such as by a microprocessor system and a set of instructions to implement the module's functionality, which (while being executed) transform the microprocessor system into a special-purpose device. A module may also be implemented as a combination of the two, with certain functions facilitated by hardware alone, and other functions facilitated by a combination of hardware and software. In certain implementations, at least a portion, and in some cases, all, of a module may be executed on the processor of a general purpose computer (such as the one described in greater detail in FIG. 16, above). Accordingly, each module may be realized in a variety of suitable configurations, and should not be limited to any particular implementation exemplified herein.

In the interest of clarity, not all of the routine features of the aspects are disclosed herein. It would be appreciated that in the development of any actual implementation of the present disclosure, numerous implementation-specific decisions must be made in order to achieve the developer's specific goals, and these specific goals will vary for different implementations and different developers. It is understood that such a development effort might be complex and time-consuming, but would nevertheless be a routine undertaking of engineering for those of ordinary skill in the art, having the benefit of this disclosure.

Furthermore, it is to be understood that the phraseology or terminology used herein is for the purpose of description and not of restriction, such that the terminology or phraseology of the present specification is to be interpreted by the skilled in the art in light of the teachings and guidance presented herein, in combination with the knowledge of the skilled in the relevant art(s). Moreover, it is not intended for any term in the specification or claims to be ascribed an uncommon or special meaning unless explicitly set forth as such.

The various aspects disclosed herein encompass present and future known equivalents to the known modules referred to herein by way of illustration. Moreover, while aspects and applications have been shown and described, it would be apparent to those skilled in the art having the benefit of this disclosure that many more modifications than mentioned above are possible without departing from the inventive concepts disclosed herein.

What is claimed is:

1. A medical device for treating emergency medical conditions, the medical device comprising:
    an ultrasound transducer configured to transmit ultrasound waves through pulmonary issue of a user and generate resulting electrical signals based on received ultrasound waves;
    a medicine release unit implanted within the body of the user, wherein the medicine release unit includes a volume of liquid medication; and
    a processing system configured to:
        determine the respiratory rate of the user based on the resulting signals that indicate a measurement of distances between emitted and reflected ultrasound pulses,
        actuate the medicine release unit to release the medication into the body of the user based on a comparison of the respiratory rate of the user with a threshold respiratory rate,
        modify the resulting electrical signals to remove signals corresponding to middle tissue reflection,
        determine a time duration between the transmitted ultrasound pulses and the reflected ultrasound pulses based on the modified signals, wherein the time duration is correlated with a lung size measurement, and
        determine the respiratory rate of the user based on the time duration and further based on a pre-determined lung size calibration.

2. The medical device of claim 1, wherein the resulting electrical signals are generated in response to detecting the ultrasound waves reflected by a lung cavity border in the body of the user.

3. The medical device of claim 1, wherein the medicine release unit includes a base valve configured to controllably release a dosage of the liquid medication through an aperture of the medicine release unit.

4. The medical device of claim 1, wherein the processor is further configured to be communicatively paired with a mobile device executing a user control application, wherein the user control application is configured to, responsive to receiving an indication of the respiratory rate of the user has reached below the threshold rate, present an option to the user via a user interface to intervene in the release of the medication.

5. The medical device of claim 4, wherein the user control application is further configured to, responsive to receiving an indication of the respiratory rate of the user has reached below the threshold rate, transmit an alert message to a pre-determined list of contacts.

6. The medical device of claim 1, wherein the liquid medication comprises an opioid antagonist for treating an opioid overdose.

7. The medical device of claim 1, further comprising:
    a light sensor configured to obtain a photoplethysmographic signal associated with the user, and
    wherein the processing system is further configured to determine the respiratory rate of the user based on the photoplethysmographic signal.

8. The medical device of claim 7, wherein the light sensor comprises:
    an infrared (IR) light-emitting source configured to emit IR light on skin surface of the user; and
    a light sensor configured to receive IR light reflected by skin surface of the user and generate a resulting photoplethysmographic signal representing variations in reflected IR light caused by varying blood volume in blood vessels of the user.

9. The medical device of claim 8, wherein the processing system is further configured to determine the respiratory rate of the user by applying wavelet decomposition to the resulting photoplethysmographic signal to remove signals corresponding to heart rate.

10. The medical device of claim 7, wherein the light sensor comprises:
    an infrared (IR) image sensor configured to generate a plurality of images of blood vessels of the user, wherein the plurality of images includes motion in the blood vessels caused by cardiac pressure pulses.

11. The medical device of claim 10, wherein the processing system is further configured to determine the respiratory rate of the user based on a photoplethysmographic signal created based on image processing of the plurality of images of the blood vessels of the user.

12. The medical device of claim 7, wherein the processing system is further configured to be communicatively paired with a mobile device executing a user control application, wherein the user control application is configured to, responsive to receiving an indication of the respiratory rate of the user has reached below the threshold rate, present an option to the user via a user interface to intervene in the release of the medication.

13. The medical device of claim 12, wherein the user control application is further configured to, responsive to receiving an indication of the respiratory rate of the user has reached below the threshold rate, transmit an alert message to a pre-determined list of contacts.

14. The medical device of claim 7, wherein the medicine release unit includes a base valve configured to controllably release a dosage of the liquid medication through an aperture of the medicine release unit.

15. The medical device of claim 7, wherein the liquid medication comprises an opioid antagonist for treating an opioid overdose.

* * * * *